United States Patent
Gibson

(10) Patent No.: US 6,809,106 B1
(45) Date of Patent: *Oct. 26, 2004

(54) QUINOLINE DERIVATIVES AS INHIBITORS OF MEK ENZYMES

(75) Inventor: Keith Hopkinson Gibson, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/959,005

(22) PCT Filed: May 3, 2000

(86) PCT No.: PCT/GB00/01707

§ 371 (c)(1),
(2), (4) Date: Oct. 17, 2001

(87) PCT Pub. No.: WO00/68200

PCT Pub. Date: Nov. 16, 2000

(30) Foreign Application Priority Data

May 8, 1999 (GB) .............................................. 9910579

(51) Int. Cl.[7] ................ A61K 31/4706; A61K 31/4709; C07D 215/44; C07D 215/38; C07D 401/12
(52) U.S. Cl. ..................... 514/311; 514/312; 514/313; 514/314; 546/153; 546/159; 546/176; 546/180
(58) Field of Search ................................ 514/311, 312, 513/313, 314; 546/153, 159, 180, 176

(56) References Cited

U.S. PATENT DOCUMENTS

| | | | |
|---|---|---|---|
| 3,376,195 A | | 4/1968 | Allais et al. |
| 3,936,461 A | | 2/1976 | Schwender et al. |
| 4,421,920 A | | 12/1983 | Baudouin |
| 4,743,601 A | * | 5/1988 | Schonafinger et al. ... 514/228.5 |
| 5,145,843 A | * | 9/1992 | Arnold et al. .............. 514/248 |
| 5,409,930 A | | 4/1995 | Spada et al. |
| 5,650,415 A | | 7/1997 | Tang et al. |
| 5,656,643 A | | 8/1997 | Spada et al. |
| RE36,256 E | | 7/1999 | Spada et al. |
| 6,002,008 A | | 12/1999 | Wissner et al. |
| 6,310,060 B1 | * | 10/2001 | Barrett et al. ............. 514/231.2 |

FOREIGN PATENT DOCUMENTS

| | | |
|---|---|---|
| EP | 0 326 330 | 8/1989 |
| FR | 2 077 455 | 10/1971 |
| WO | 87/04321 | 7/1987 |
| WO | 93/03030 | 2/1993 |
| WO | 96/09294 | 3/1996 |
| WO | 97/03069 | 1/1997 |
| WO | 97/17329 | 5/1997 |
| WO | 98/02434 | 1/1998 |
| WO | 98/13350 | 4/1998 |
| WO | WO 99/01421 | 1/1999 |
| WO | WO 99/01426 | 1/1999 |
| WO | 99/35146 | 7/1999 |
| WO | WO 98/43960 | 10/1999 |
| WO | 00/18740 | 4/2000 |
| WO | 00/18761 | 4/2000 |

OTHER PUBLICATIONS

Hagemann C et al. Cellular Signalling. 2001, 13(12), 863–75.*
U.S. patent application Ser. No. 09/254,440, Thomas, filed Mar. 9, 1999.
U.S. patent application Ser. No. 09/959,813, Boyle et al., filed Nov. 8, 2001.
U.S. patent application Ser. No. 09/913,864, Crawley et al., filed Aug. 20, 2001.
U.S. patent application Ser. No. 09/959,434, Gibson et al., filed Oct. 25, 2001.

(List continued on next page.)

Primary Examiner—Evelyn Mei Huang
(74) Attorney, Agent, or Firm—Morgan Lewis & Bockius LLP

(57) ABSTRACT

A compound of formula (I)

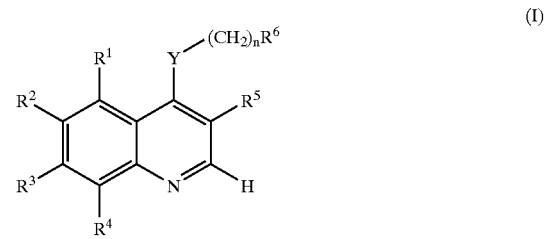

or a pharmaceutically acceptable salt thereof; for use as a medicament wherein:

n is 0–1;

Y is selected from —NH—, —O—, —S—, or —NR[7]— where R[7] is alkyl of 1–6 carbon atoms R[5] is chloro or bromo;

Y is selected from —NH—, —O—, —S—, or —NR[7]— where R[7] is alkyl of 1–6 carbon atoms R[6] is a specified cyclic group which may be substituted by various specified substituents, or R[6] is a group —R[8]—X—R[9] where R[8] is selected from various cycloalkyl, pyridinyl, pyimidinyl, or phenyl ring; any of which may be optionally subsituted as described, where X is selected from CH$_2$, —NH—, —O—, —S—, CH$_2$ or —NR[5]— where R[5] is alkyl of 1–6 carbon atoms, and R[9] is a group (CH$_2$)$_m$R[10] where m is 0, or an integer of from 1–3 and R[10] is an optionally substituted aryl or optionally substituted cycloalkyl ring of up to 10 carbon atoms, or R[10] is a heterocyclic ring containing 1 or 2 oxygen atoms and optionally one or more substitutents; and R[1], R[2], R[3] and R[4] are each independently selected from hydrogen or various specified organic groups. Novel compounds are also described. The compounds are particularly useful in the inhibition of MEK enzymes.

7 Claims, No Drawings

OTHER PUBLICATIONS

Atkins et al., "Synthetic Routes to Quinoline Derivatives: Novel Syntheses of 3–Butyryl–8–methoxy–4–[(2–methylphenyl)amino]quinoline and 3–Butyryl–8–(2–hydroxyethoxy)–4–[(2–methylphenyl)amino]quinoline", Org. Process Res Dev. vol. 1(3), 1997, pp. 185–197, XP000986311.

Ife et al., Reversible Inhibitors of the Gastric ($H^+/K^+$)–ATPase. 3. 3–Substituted–4–(phenylamino)quinolines, J. Med. Chem., 199, 35, pp. 3413–3422.

Chemical Abstracts, vol. 122, No. 21, May 22, 1995 Columbus, Ohio, US; abstract No. 264686k, Wyszomirski, Miroslaw et al.: "Conformation of monosubstituted and disubstituted 3,4'–, 3,3'–and 4,4'–diquinolyl sulfides studied by NMR spectroscopy" XP002146785 abstract & Database Chemical Abstracts Online ! CA 122:264686; xp002146786 compound with RN 162662–34–2 & phosphorus, sulfur silicon relat. elem., vol. 95 & 96, No. 1–4, –1994 p. 415–416.

* cited by examiner

QUINOLINE DERIVATIVES AS INHIBITORS OF MEK ENZYMES

This application is the National Phase of International Application PCT/GB00/01707 filed May 3, 2000 which designated the U.S. and that International Application was published under PCT Article 21(2) in English.

The present invention relates to certain novel quinoline derivatives as well as to their use as pharmaceuticals, in particular as inhibitors of specific kinase enzymes, in particular MEK enzymes. Further aspects of the invention include pharmaceutical compositions and methods of treatment of proliferative disease such as cancer using said compounds.

Cancer is a disease in which cells grow and divide in an uncontrolled fashion. This uncontrolled growth arises from abnormalities in signal transduction pathways that are used by normal cells to regulate cell growth and division in response to various signalling molecules. Normal cells do not proliferate unless stimulated to do so by specific signal molecules located outside the cell derived from nearby cells or tissues. Growth factors bind to the cell membrane via specific receptors which have intrinsic enzyme activity. These receptors relay the growth signal to the cell nucleus via a series of signalling proteins. In cancer, a number of defects in signal pathways are apparent. For example, cancer cells may produce their own growth factors which bind to their cognate receptors, resulting in an autocrine loop, or receptors may be mutated or overexpressed leading to an increased, continuous signal to proliferate. In addition, negative regulators of cell growth may be lost.

Oncogenes are cancer related genes which often encode abnormal versions of signal pathway components, such receptor tyrosine kinases, serine-threonine kinasem or downstream signaling molecules such as the ras genes, which code for closely related small guanine nucleotide binding proteins which hydrolyse bound guanosine triphosphate (GTP) to guanosine diphosphate (GDP). Ras proteins are active in promoting cell growth and transformation when they are bound to GTP and inactive when they are bound to GDP. Transforming mutants of p21ras are defective in their GTPase activity and hence remain in the active GTP bound state. The ras oncogene is known to play an integral role in certain cancers, and has been found to contribute to the formation of over 20% of all cases of human cancer.

When activated by ligand, cell surface receptors which are coupled to the mitogenic response, such as growth factor receptors, initiate a chain of reactions which leads to the activation of guanine nucleotide exchange activity on ras. When in its active GTP-bound state, a number of proteins interact directly with ras at the plasma membrane resulting in signal transmission through several distinct pathways. The best characterised effector protein is the product of the raf proto-oncogene. The interaction of raf and ras is a key regulatory step in the control of cell proliferation. Ras-mediated activation of the raf serine-threonine kinase in turn activates the dual-specificity MEK (MEK1 and MEK2), which is the immediate upstream activator of mitogen activated protein kinase (MAPKs known as extracellular signal regulated protein kinases or ERK1 and ERK2). To date, no substrates of MEK other than MAPK have been identified, though recent reports indicate that MEK may also be activated by other upstream signal proteins such as MEK kinase or MEKK1 and PKC. Activated MAPK translocates and accumulates in the nucleus, where it can phosphorylate and activate transcription factors such as Elk-1 and Sap1a, leading to the enhanced expression of genes such as that for c-fos.

The ras-dependent raf-MEK-MAPK cascade is one of the key signalling pathways responsible for transmitting and amplifying mitogenic signals from cell surface to the nucleus resulting in changes in gene expression and cell fate. This ubiquitous pathway appears essential for normal cell proliferation and constitutive activation of this pathway is sufficient to induce cellular transformation. Transforming mutants of p21ras are constitutively active, resulting in raf, MEK and MAPK activity and cell transformation. Inhibition of MEK activity using either antisense raf, a dominant negative MEK mutant or the selective inhibitor PD098059 have been shown to block the growth and morphological transformation of ras-transformed fibroblasts.

The mechanism of activation of raf, MEK and MAPK is through phosphorylation on specific serene, threonine or tyrosine residues. Activated raf and other kinases phosphorylate MEK1 on S218 and S222 and MEK2 on S222 and S226. This results in MEK activation and subsequent phosphorylation and activation of ERK1 on T190 and Y192 and ERK2 on T183 and Y185 by the dual specificity MEKs. Whilst MEK can be activated by a number of protein kinases, and active MAPKs phosphorylate and activate a number of substrate proteins including transcription factors and other protein kinases, MEKs appear specific and sole activators of MAPKs and could act as a focal point for cross-cascade regulation. MEK1 and MEK2 isoforms show unusual specificity and also contain a proline-rich insert between catalytic subdomains IX and X which is not present in any of the other known MEK family members. These differences between MEK and other protein kinases, together with the known role of MEK in proliferative signalling suggest that it may be possible to discover and employ selective MEK inhibitors as therapeutic agents for use in proliferative disease.

WO 98/43960 discloses a range of 3-cyano quinoline compounds and their use in the treatment of cancer. Certain of the compounds are demonstrated as being inhibitors of Epidermal Growth Factor Receptor Kinase, and to inhibit cancer cell growth. Other quinoline derivatives which inhibit the effect of growth factors such as VEGF are described in WO98/13350.

The conformations of certain diquinolinyl sulfides have been studied by NMR and reported by Wyszomirski et al in Phosphorus, Sulphur and Silicon, 1994, vol 95–96, pg 415–416. Methods of making specific quinoline derivatives are described by Atkins et al in Organic Process Research and Development, 1997, vol 1, pg 185–197. The use of certain quinoline derivatives as gastric ($H^+/K^+$)—ATPase inhibitors and as fungicides are described by Ife et al in J Med Chem, 1992, vol 35, pg 3413–3422 and in EP 326330 respectively.

This invention provides compounds which are inhibitors of the kinase activity of MEK and as a result, can produce therapeutically useful effects in the treatment of proliferative disease and in particular cancer.

According to the present invention there is provided a compound of formula (I)

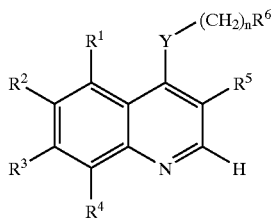

(I)

or a pharmaceutically acceptable salt thereof; for use as a medicament wherein:

n is 0–1;

Y is selected from —NH—, —O—, —S—, or —NR$^7$— where R$^7$ is alkyl of 1–6 carbon atoms R$^5$ is chloro or bromo;

Y is selected from —NH—, —O—, —S—, or —NR$^7$— where R$^7$ is alkyl of 1–6 carbon atoms R$^6$ is cycloalkyl of 3 to 7 carbon atoms, which may be optionally substituted with one or more alkyl of 1 to 6 carbon atom groups; or is a pyridinyl, pyrimidinyl, or phenyl ring;

wherein the pyridinyl, pyrimidinyl, or phenyl ring may be substituted with one, two or three groups selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenyl, benzoyl, amino, alkylamino of 1–6 carbon atoms, dialkylamino of 2 to 12 carbon atoms, alkanoylamino of 1–6 carbon atoms, alkenoylamino of 3–8 carbon atoms, alkynoylamino of 3–8 carbon atoms, and benzoylamino; or two adjacent substitutents on said phenyl, pyridyl or pyrimidinyl ring may be joined together to form a fused ring, which ring may be aromatic or non-aromatic in character and which may contain further heteroatoms;

or R$^6$ is a group —R$^8$—X—R$^9$ where

R$^8$ is a divalent cycloalkyl of 3 to 7 carbon atoms, which may be optionally further substituted with one or more alkyl of 1 to 6 carbon atom groups; or is a divalent pyridinyl, pyimidinyl, or phenyl ring; wherein the pyridinyl, pyrimidinyl, or phenyl ring may be optionally further substituted with one or more groups selected from halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino;

where X is selected from CH$_2$, —NH—, —O—, —S—, CH$_2$ or —NR$^5$— where R$^5$ is alkyl of 1–6 carbon atoms, and R$^9$ is a group (CH$_2$)$_m$R$^{10}$ where m is 0, or an integer of from 1–3 and R$^{10}$ is an optionally substituted aryl or optionally substituted cycloalkyl ring of up to 10 carbon atoms, or R$^{10}$ is a heterocyclic ring containing 1 or 2 oxygen atoms and optionally one or more substitutents; R$^1$, R$^2$, R$^3$ and R$^4$ are each independently selected from hydrogen, hydroxy, halogeno, cyano, nitro, trifluoromethyl, $C_{1-3}$alkyl, —NR$^{11}$R$^{12}$ (wherein R$^{11}$ and R$^{12}$, which may be the same or different, each represents hydrogen or $C_{1-3}$alkyl), or a group R$^{13}$—X$^1$—(CH$_2$)$_x$ wherein x is 0 to 3, X$^1$ represents —O—, —CH$_2$—, —OCO—, carbonyl, —S—, —SO—, —SO$_2$—, —NR$^{14}$CO—, —CONR$^{15}$—, —SO$_2$NR$^{16}$—, —NR$^{17}$SO$_2$— or —NR$^{18}$— (wherein R$^{14}$, R$^{15}$, R$^{16}$, R$^{17}$ and R$^{18}$ each independently represents hydrogen, $C_{1-3}$alkyl or $C_{1-3}$alkoxy$C_{2-3}$alkyl) and R$^{13}$ is selected from one of the following sixteen groups:

1) $C_{1-5}$alkyl which may be unsubstituted or which may be substituted with one or more groups selected from hydroxy, fluoro and amino;

2) $C_{1-5}$alkylX$^2$COR$^{19}$ (wherein X$^2$ represents —O— or —NR$^{20}$— (wherein R$^{20}$ represents hydrogen, $C_{1-3}$alkyl or $C_{1-3}$alkoxy$C_{2-3}$alkyl) and R$^{19}$ represents —NR$^{21}$R$^{22}$— or —OR$^{23}$— (wherein R$^{21}$, R$^{22}$ and R$^{23}$ which may be the same or different each represents hydrogen, $C_{1-3}$alkyl or $C_{1-3}$alkoxy$C_{2-3}$alkyl));

3) $C_{1-5}$alkylX$^3$R$^{24}$ (wherein X$^3$ represents —O—, —S—, —SO—, —SO$_2$—, —OCO—, —NR$^{25}$CO—, —CONR$^{26}$—, —SO$_2$NR$^{27}$—, —NR$^{28}$SO$_2$— or —NR$^{29}$— (wherein R$^{25}$, R$^{26}$, R$^{27}$, R$^{28}$ and R$^{29}$ each independently represents hydrogen, $C_{1-3}$alkyl or $C_{1-3}$alkoxy$C_{2-3}$alkyl) and R$^{24}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-4}$alkoxy and which cyclic group may bear one or two substituents selected from oxo, hydroxy, halogeno, $C_{1-4}$alkyl, $C_{1-4}$hydroxyalkyl and $C_{1-4}$alkoxy);

4) $C_{1-5}$alkylX$^4C_{1-5}$alkylX$^5$R$^{30}$ (wherein X$^4$ and X$^5$ which may be the same or different are each —O—, —S—, —SO—, —SO$_2$—, —NR$^{31}$CO—, —CONR$^{32}$—, —SO$_2$NR$^{33}$—, —NR$^{34}$SO$_2$— or —NR$^{35}$— (wherein R$^{31}$, R$^{32}$, R$^{33}$, R$^{34}$ and R$^{35}$ each independently represents hydrogen, $C_{1-3}$alkyl or $C_{1-3}$alkoxy$C_{2-3}$alkyl) and R$^{30}$ represents hydrogen or $C_{1-3}$alkyl);

5) $C_{1-5}$alkylR$^{36}$ (wherein R$^{36}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy);

6) (CH$_2$)$_q$X$^6$R$^{37}$ (wherein q is an integer from 0 to 5, X$^6$ represents a direct bond, —O—, —S—, —SO—, —SO$_2$—, —NR$^{38}$CO—, CONR$^{39}$—, —SO$_2$NR$^{40}$—, —NR$^{41}$SO$_2$— or —NR$^{42}$— (wherein R$^{38}$, R$^{39}$, R$^{40}$, R$^{41}$ and R$^{42}$ each independently represents hydrogen, $C_{1-3}$alkyl or $C_{1-3}$alkoxy$C_{2-3}$alkyl) and R$^{37}$ is a phenyl group, a pyridone group or a 5 or 6 membered aromatic heterocyclic group with 1 to 3 heteroatoms selected from O, N and S, which phenyl, pyridone or aromatic heterocyclic group may carry up to 5 substituents selected from hydroxy, halogeno, amino, $C_{1-4}$alkyl, $C_{1-4}$alkoxy, $C_{1-4}$hydroxyalkyl, $C_{1-4}$hydroxyalkoxy, $C_{1-4}$aminoalkyl, $C_{1-4}$alkylamino, carboxy, cyano, —CONR$^{43}$R$^{44}$ and —NR$^{45}$COR$^{46}$ (wherein R$^{43}$, R$^{44}$, R$^{45}$ and R$^{46}$, which may be the same or different, each represents hydrogen, $C_{1-4}$alkyl or $C_{1-3}$alkoxy$C_{2-3}$alkyl));

7) $C_{2-6}$alkenylR$^{36}$ (wherein R$^{36}$ is as defined hereinbefore);

8) $C_{2-6}$alkynylR$^{36}$ (wherein R$^{36}$ is as defined hereinbefore);

9) $X^7R^{47}$ (wherein $X^7$ is —$SO_2$—, —O— or —$CONR^{48}R^{49}$— (wherein $R^{48}$ and $R^{49}$, which may be the same or different, each represents hydrogen, $C_{1-3}$alkyl or $C_{1-3}$alkoxy$C_{2-3}$alkyl) and $R^{47}$ represents $C_{1-5}$alkyl which may be unsubstituted or which may be substituted with one or more groups selected from hydroxy, fluoro and amino) with the provisos that when $X^7$ is —$SO_2$—, $X^1$ is —O—, when $X^7$ is —O—, $X^1$ is carbonyl, when $X^7$ is —$CONR^{48}R^{49}$—, $X^1$ is —O— or $NR^{18}$ (wherein $R^{48}$, $R^{49}$ and $R^{18}$ are as defined hereinbefore);
10) $C_{2-6}$alkenyl$R^{37}$ (wherein $R^{37}$ is as defined hereinbefore);
11) $C_{2-6}$alkynyl$R^{37}$ (wherein $R^{37}$ is as defined hereinbefore);
12) $C_{2-6}$alkenyl$X^8R^{37}$ (wherein $X^8$ represents —O—, —S—, —SO—, —$SO_2$—, —$NR^{50}CO$—, —$CONR^{51}$—, —$SO_2NR^{52}$—, —$NR^{53}SO_2$— or —$NR^{54}$— (wherein $R^{50}$, $R^{51}$, $R^{52}$, $R^{53}$ and $R^{54}$ each independently represents hydrogen, $C_{1-3}$alkyl or $C_{1-3}$ alkoxy$C_{1-3}$alkyl) and $R^{37}$ is as defined hereinbefore);
13) $C_{2-6}$alkynyl$X^9R^{37}$ (wherein $X^9$ represents —O—, —S—, —SO—, —$SO_2$—, —$NR^{55}CO$—, —$CONR^{56}$—, —$SO_2NR^{57}$—, —$NR^{58}SO_2$— or —$NR^{59}$— (wherein $R^{55}$, $R^{56}$, $R^{57}$, $R^{58}$ and $R^{59}$ each independently represents hydrogen, $C_{1-3}$alkyl or $C_{1-3}$alkoxy$C_{2-3}$alkyl) and $R^{37}$ is as defined hereinbefore);
14) $C_{1-3}$alkyl$X^{10}C_{1-3}$alkyl$R^{37}$ (wherein $X^{10}$ represents —O—, —S—, —SO—, —$SO_2$—, —$NR^{60}CO$—, —$CONR^{61}$—, —$SO_2NR^{62}$—, —$NR^{63}SO_2$— or —$NR^{64}$— (wherein $R^{60}$, $R^{61}$, $R^{62}$, $R^{63}$ and $R^{64}$ each independently represents hydrogen, $C_{1-3}$alkyl or $C_{1-3}$alkoxy$C_{2-3}$alkyl) and $R^{37}$ is as defined hereinbefore);
15) $R^{36}$ (wherein $R^{36}$ is as defined hereinbefore; and
16) $C_{1-3}$alkyl$X^{10}C_{1-3}$alkyl$R^{36}$ (wherein $X^{10}$ and $R^{36}$ are as defined hereinbefore).

In particular the invention provides a compound of formula (I) as shown above or a pharmaceutically acceptable salt thereof; for use as a medicament wherein:
n is 0–1;
Y is selected from —NH—, —O—, —S—, or —$NR^7$— where $R^7$ is alkyl of 1–6 carbon atoms
$R^5$ is chloro or bromo;
Y is selected from —NH—, —O—, —S—, or —$NR^7$— where $R^7$ is alkyl of 1–6 carbon atoms
$R^6$ is cycloalkyl of 3 to 7 carbon atoms, which may be optionally substituted with one or more alkyl of 1 to 6 carbon atom groups; or is a pyridinyl, pyrimidinyl, or phenyl ring;
wherein the pyridinyl, pyrimidinyl, or phenyl ring may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of3–8 carbon atoms, and benzoylamino;
or $R^6$ is a group —$R^8$—X—$R^9$ where
$R^8$ is a divalent cycloalkyl of 3 to 7 carbon atoms, which may be optionally further substituted with one or more alkyl of 1 to 6 carbon atom groups; or is a divalent pyridinyl, pyimidinyl, or phenyl ring; wherein the pyridinyl, pyrimidinyl, or phenyl ring may be optionally further substituted with one or more groups selected from halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino;
where X is selected from —NH—, —O—, —S—, $CH_2$ or —$NR^a$— where $R^a$ is alkyl of 1–6 carbon atoms, and
$R^9$ is a group $(CH_2)_mR^{10}$ where m is 0, or an integer of from 1–3 and $R^{10}$ is an optionally substituted aryl or optionally substituted cycloalkyl ring of up to 10 carbon atoms, or $R^{10}$ is a heterocyclic ring containing 1 or 2 oxygen atoms and optionally one or more substituents;
$R^1$, $R^2$, $R^3$ and $R^4$ are each independently selected from hydrogen, hydroxy, halogeno, cyano, nitro, trifluoromethyl, $C_{1-3}$alkyl, —$NR^{11}R^{12}$ (wherein $R^{11}$ and $R^{12}$, which may be the same or different, each represents hydrogen or $C_{1-3}$alkyl), or a group $R^{13}$—$X^1$—$(CH_2)_x$ wherein x is 0 to 3, $X^1$ represents —O—, —$CH_2$—, —OCO—, carbonyl, —S—, —SO—, —$SO_2$—, —$NR^{14}CO$—, —$SO_2NR^{16}$—, —$NR^{17}SO_2$— or —$NR^{18}$— (wherein $R^{14}$, $R^{15}$, $R^{16}$, $R^{17}$ and $R^{18}$ each independently represents hydrogen, $C_{1-3}$alkyl or $C_{1-3}$alkoxy$C_{2-3}$alkyl) and $R^{13}$ is selected from one of the sixteen groups defined above.

Suitable pharmaceutically acceptable salts of compounds of formula (I) include acid addition salts such as methanesulfonate, fumarate, hydrochloride, hydrobromide, citrate, maleate and salts formed with phosphoric and sulphuric acid. A preferred pharmaceutically acceptable salt is a hydrochloride salt.

The alkyl portion of the alkyl, alkoxy, alkanoyloxy, alkoxymethyl, alkanoyloxymethyl, alkylsuphinyl, alkylsulphonyl, alkylsulfonamido, carboalkoxy, carboalkyl, alkanoylamino aminoalkyl, alkylaminoalkyl, N,N-dicycloalkylaminoalkyl, hydroxyalkyl, and alkoxyalkyl substituents include both straight chain as well as branched carbon chains. The cycloalkyl portions of N-cycloalkyl-N-alkylaminoalkyl and N,N-dicycloalkylaminoalkyl substituents include both simple carbocycles as well as carbocycles containing alkyl substituents. The alkenyl portion of the alkenyl, alkenoyloxymethyl, alkenyloxy, alkenylsulfonamido, substituents include both straight chain as well as branched carbon chains and one or more sites of unsaturation. The alkynyl portion of the alkynyl, alkynoyloxymethyl, alkynylsulfonamido, alkynyloxy, substituents include both straight chain as well as branched carbon chains and one or more sites of unsaturation. Carboxy is defined as a —$CO_2H$ radical. Carboalkoxy of 2–7 carbon atoms is defined as a —$CO_2R"$ radical, where R" is an alkyl radical of 1–6 carbon atoms. Carboalkyl is defined as a —COR" radical, where R" is an alkyl radical of 1–6 carbon atoms. Alkanoyloxy is defined as a —OCOR" radical, where R" is an alkyl radical of 1–6 carbon atoms. Alkanoyloxymethyl is defined as R"$CO_2CH_2$— radical, where R" is an alkyl radical of 1–6 carbon atoms. Alkoxymethyl is defined at R"$OCH_2$— radical, where R" is an alkyl radical of 1–6 carbon atoms. Alkyl sulphinyl is defined as R"SO— radical, where R" is an alkyl radical of 1–6 carbon atoms. Alkylsulphonyl is defined as R"SO$_2$— radical, where R" is alkyl radical of 1–6 carbon atoms. Alkylsulfonamido, alkenylsulfonamido, alkynylsulfonamido are defined as R"SO$_2$NH— radical, where R" is an alkyl radical of 1–6 carbon atoms, an alkenyl radical of 2–6 carbon atoms, or an alkynyl radical of 2–6 carbon atoms, respectively. N-alkylcarbamoyl is defined as R"NHCO— radical, where R" is an alkyl radical of 1–6 carbon atoms. N,N-dialkylcarbamoyl is defined as R" R'NCO— radical, where R" is an alkyl radical of 1–6 carbon atoms, R' is an alkyl radical of 1–6 carbon atoms and R', and R" may be the same or different. When X is substituted, it is preferred that it is mono-, di-, or tri-substituted, with monosubstituted being most preferred. It is preferred that of the substituents, $R_1$, $R_2$, $R_3$ and $R_4$ at least one is hydrogen and it is most preferred that two or three be hydrogen. An azacycloalkyl-N-alkyl substituent refers to a monocyclic heterocycle that contains a nitrogen atom on which is substituted a straight or branched chain alkyl radical. A morpholino-N-alkyl substituent is a morpholine ring substituted on the nitrogen atom with a straight or branch chain alkyl radical. A piperidino-N-alkyl substituent is a piperidine ring substituted on one of the nitrogen atoms with a straight or branch chain alkyl radical. A N-alkyl-piperazino-N-alkyl substituent is a piperazine ring substituted on one of the nitrogen atoms with a straight or branched chain alkyl group and on the other nitrogen atom with a straight or branch chain alkyl radical.

When any group contains an alkyl portion, the alkyl portion contains preferably 1–6 carbon atoms, more preferably 1–4 carbon atoms, particularly methyl, ethyl, n-propyl iso-propyl, n-butyl, iso-butyl, sec-butyl or tert-butyl. When any group contains an alkenyl or alkynyl portion, the alkenyl or alkynyl portion contains preferably 2–6 carbon atoms, more preferably 2–4 carbon atoms.

The term "aryl" used herein includes aromatic carbocyclic compounds, for example of from 6 to 20 atoms such as phenyl or naphthyl. The term "heterocyclic" refers to ring structures suitably from 5 to 20 atoms in size, up to four of which are heteroatoms such as oxygen, sulphur and nitrogen. The ring structures may be monocyclic, bi- or tricyclic and be aromatic or non-aromatic in character including the possibility that part of a ring system has aromatic character whilst other part(s) do not.

The compounds of this invention may contain an asymmetric carbon; in such cases, the compounds of this invention cover the racemate and the individual R and S entantiomers, and in the case where more than one asymmetric carbon exists, the individual diasteromers, their racemates and individual entantiomers.

Preferably Y is —NH—.

Preferably $R^5$ is chloro.

Suitably $R^a$ is phenyl, pyridyl or pyrimidinyl, and preferably phenyl which are optionally substituted as defined above. Suitable substituents include halo such as chloro or fluoro, hydroxy or benzoyl.

When two adjacent substitutents on said phenyl, pyridyl or pyrimidinyl ring are be joined together to form a fused ring, the ring is suitably a 5 or 6 membered aromatic ring, and preferably a 5 membered ring which includes at least one heteroatom such as nitrogen. Particular examples of groups $R^a$ are indole, benzimidazole, or indazole.

In a preferred embodiment, the group $R^6$ is a group —$R^8$—X—$R^9$ where $R^8$, X and $R^9$ are as defined above. Suitably X is oxygen.

Preferably n is 0.

Examples of optional substituents for groups $R^{10}$ include one or more groups selected from hydroxy; halo; nitro; cyano; carboxy; $C_{1-6}$alkoxy; $C_{1-6}$alkyl; $C_{2-6}$alkenyl; $C_{2-6}$alkynyl; $C_{2-6}$alkenyloxy; $C_{2-6}$alkynyloxy; $C_{3-6}$cycloalkyl; amino; mono- or di-$C_{1-6}$alkyl amino; heterocyclyl optionally substituted with $C_{1-4}$alkyl or oxo; C(O)$R^a$, C(O)O$R^a$, S(O)$_d R^{a;}$ $NR^a$C(O)$R^b$; C(O)NR$^a$S(O)$_d R^b$, C(O)NR$^a R^{b;}$; NR$^a$C(O)NR$^b R^c$; NR$^a$S(O)$_d R^b$ or N(S(O)$_d R^b$)S(O)$_d R^c$ where d is 0, 1 or 2 and $R^a$, $R^b$ and $R^c$ are independently selected from hydrogen, $C_{1-6}$alkyl, aryl, $C_{3-6}$cycloalkyl or heterocylcyl, and wherein any alkyl, alkenyl or alkynyl group or moiety contained within the substituent one $R^{10}$ may themselves be optionally substituted with one or more groups selected from hydroxy; cyano; nitro; halo; carboxy; carboalkoxy of 2–7 carbon atoms, $C_{3-6}$cycloalkyl, heterocyclyl optionally substituted with $C_{1-6}$alkyl or oxo; C(O)$R^d$, C(O)O$R^d$NR$^d R^e$, S(O)$_e R^d$, NR$^d$C(O)$R^e$; C(O)NR$^d R^e$; NR$^d$C(O)NR$^e R^f$; NR$^d$S(O)$_e R^e$ where e is 0, 1 or 2 and $R^d$, $R^e$ and $R^f$ are independently selected from hydrogen or $C_{1-6}$alkyl optionally substituted with one or more groups selected from hydroxy; cyano; nitro; halo; carboxy; carboalkoxy of 2–7 carbon atoms, $C_{3-4}$cycloalkyl, heterocyclyl optionally substituted with $C_{1-6}$alkyl or oxo; C(O)$R^g$, C(O)O$R^g$NR$^g R^h$, S(O)$_e R^g$, NR$^h$C(O)$R^g$; C(O)NR$^g R^h$; NR$^g$C(O)NR$^h R^i$; NR$^g$S(O)$_e R^h$ where e is as defined above and $R^g$, $R^h$ and $R^i$ are independently selected from hydrogen or $C_{1-6}$alkyl. Alternatively, two substituents on adjacent atoms may be joined to form the second ring of a bicyclic ring system wherein the said second ring is optionally substituted with one or more of the groups listed above for $R^{10}$ and optionally contains one or more heteroatoms.

In some embodiments, the level of substitution on the group $R^{10}$ is a chain substituted with a complex substituent. Thus, for example, a substituent may comprise an subsituted alkyl chain which is optionally interposed with heteroatoms such as groups of sub-formula (i)

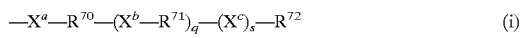

$$-X^a-R^{70}-(X^b-R^{71})_q-(X^c)_s-R^{72} \qquad (i)$$

where $X^a$, $X^b$ and $X^c$ are independently selected from any of the groups listed above for X', $R^{70}$ and $R^{71}$ are independently selected from $C_{1-4}$alkylene, $C_{2-4}$alkenylene or $C_{2-4}$alkynylene groups any of which may be optionally substituted with hydroxy; cyano; nitro; halo; carboxy, carboalkoxy of 2–7 carbon atoms or $C_{3-4}$cycloalkyl;

$R^{72}$ is hydrogen or an $C_{1-4}$alkyl, $C_{2-4}$ alkenyl or $C_{2-4}$alkynyl group any of which may be optionally substituted with hydroxy; cyano; nitro; halo; carboxy or $C_{3-4}$cycloalkyl;

and q and s are independently 0 or 1.

Particular examples of groups $R^{10}$ include phenyl or cycloalkyl of from 3–8 and preferably of 6 carbon atoms which are substituted at the position alpha with a alkoxy group, in particular methoxy.

When $R^{10}$ is substituted phenyl or cycloalkyl, m is preferably 0.

Examples of heterocyclic rings $R^{10}$ include 3–7 membered rings, up to two of which may be oxygen atoms. Such groups include:

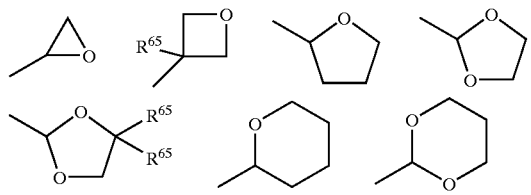

-continued

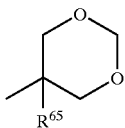

where each $R^{65}$ is independently selected from hydrogen or $C_{1-6}$alkyl and especially methyl. In such compounds, m is suitably 1, 2 or 3.

Suitable further substituents for $R^8$ include those listed above for pyridyl, pyrimidinyl and phenyl groups $R^{6\cdot}$ Thus a preferred sub-group of compounds of formula (I) are compounds of formula (II)

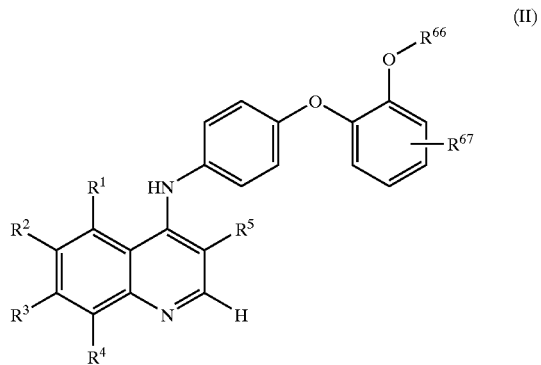

(II)

where $R^1$, $R^2$, $R^3$, $R^4$ and $R^5$ are as defined above and $R^{66}$ is $C_{1-6}$ alkyl in particular methyl and $R^{67}$ is selected from hydrogen, halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino.

Preferably $R^{67}$ is hydrogen.

Examples of preferred groups for $R^1$, $R^2$, $R^3$ and $R^4$ are set out in WO 98/13350. Preferably x is 0. Conveniently $R^{13}$ is selected from one of the following sixteen groups:

1) $C_{1-5}$alkyl which may be unsubstituted or substituted with one or more fluorine atoms, or $C_{2-5}$alkyl which may be unsubstituted or substituted with one or more groups selected from hydroxy and amino;
2) $C_{2-3}$alkylX$^2$COR$^{19}$ (wherein $X^2$ is as defined hereinbefore and $R^{19}$ represents —NR$^{21}$R$^{22}$— or —OR$^{23}$— (wherein $R^{21}$, $R^{22}$ and $R^{23}$ which may be the same or different each represents hydrogen, $C_{1-2}$alkyl or $C_{1-2}$alkoxyethyl));
3) $C_{2-4}$alkylX$^3$R$^{24}$ (wherein $X^3$ is as defined hereinbefore and $R^{24}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-3}$alkoxy and which cyclic group may bear one or two substituents selected from oxo, hydroxy, halogeno, $C_{1-3}$alkyl, $C_{1-3}$hydroxyalkyl and $C_{1-3}$alkoxy);
4) $C_{2-3}$alkylX$^4$C$_{2-3}$alkylX$^5$R$^{30}$ (wherein $X^4$ and $X^5$ are as defined hereinbefore and $R^{30}$ represents hydrogen or $C_{1-3}$alkyl);
5) $C_{1-5}$alkylR$^{70}$ (wherein $R^{70}$ is a 5 or 6 membered saturated heterocyclic group with one or two heteroatoms, selected independently from O, S and N, which heterocyclic group is linked to $C_{1-5}$alkyl through a carbon atom and which heterocyclic group may bear one or two substituents selected from oxo, hydroxy, halogeno, $C_{1-3}$alkyl, $C_{1-3}$hydroxyalkyl and $C_{1-3}$alkoxy) or $C_{2-5}$alkylR$^{71}$ (wherein $R^{71}$ is a 5 or 6 membered saturated heterocyclic group with one or two heteroatoms of which one is N and the other is selected independently from O, S and N, which heterocyclic group is linked to $C_{2-5}$alkyl through a nitrogen atom and which heterocyclic group may bear one or two substituents selected from oxo, hydroxy, halogeno, $C_{1-3}$alkyl, $C_{1-3}$hydroxyalkyl and $C_{1-3}$alkoxy);
6) $(CH_2)_qX^6R^{37}$ (wherein $X^6$ is as defined hereinbefore; q is an integer from 0 to 4 if $X^6$ is a direct bond and q is 0, 2 or 3 if $X^6$ is other than a direct bond; and $R^{37}$ is a phenyl group, a pyridone group or a 5 or 6 membered aromatic heterocyclic group with 1 to 3 heteroatoms selected from O, N and S, of which preferably one is N, which phenyl group, pyridone group or aromatic heterocyclic group may be substituted as hereinbefore defined, advantageously substituted with up to 2 substituents as hereinbefore defined, more preferably substituted with one substituent selected from the group of substituents as hereinbefore defined);
7) $C_{4-5}$alkenylR$^{72}$ (wherein $R^{72}$ represents $R^{70}$ or $R^{71}$ as defined hereinbefore);
8) $C_{4-5}$alkylR$^{72}$ (wherein $R^{72}$ represents $R^{70}$ or $R^{71}$ as defined hereinbefore);
9) $X^7R^{47}$ (wherein $X^7$ is as defined hereinbefore and $R^{47}$ represents $C_{1-3}$alkyl which may be unsubstituted or which may be substituted with one or more groups selected from hydroxy, fluoro and amino);
10) $C_{3-5}$alkenylR$^{37}$ (wherein $R^{37}$ is as defined hereinbefore);
11) $C_{3-5}$alkynylR$^{37}$ (wherein $R^{37}$ is as defined hereinbefore);
12) $C_{4-5}$alkenylX$^8$R$^{37}$ (wherein $X^8$ and $R^{37}$ are as defined hereinbefore);
13) $C_{4-5}$alkynylX$^9$R$^{30}$ (wherein $X^9$ and $R^{30}$ are as defined hereinbefore);
14) $C_{1-3}$alkylX$^{10}$C$_{1-3}$alkylR$^{37}$ (wherein $X^{10}$ and $R^{37}$ are as defined hereinbefore);
15) $R^{36}$ (wherein $R^{36}$ is as defined hereinbefore); and
16) $C_{1-3}$alkylX$^{11}$C$_{1-3}$alkylR$^{36}$ (wherein $X^{11}$ and $R^{36}$ are as defined hereinbefore).

Advantageously $R^{13}$ is selected from one of the following eleven groups:

1) $C_{1-4}$alkyl which may be unsubstituted or substituted with one or more fluorine atoms, or $C_{2-4}$alkyl which may be unsubstituted or substituted with one or two groups selected from hydroxy and amino;
2) $C_{2-3}$alkylX$^2$COR$^{19}$ (wherein $X^2$ is as defined hereinbefore and $R^{19}$ represents —NR$^{21}$R$^{22}$— or —OR$^{23}$— (wherein $R^{21}$, $R^{22}$ and $R^{23}$ which may be the same or different each represents hydrogen, $C_{1-2}$alkyl or $C_{1-2}$alkoxyethyl));
3) $C_{2-3}$alkylX$^3$R$^{24}$ (wherein $X^3$ is as defined hereinbefore and $R^{24}$ is a group selected from $C_{1-3}$alkyl, cyclopentyl, cyclohexyl, pyrrolidinyl and piperidinyl which group is linked to $X^3$ through a carbon atom and which $C_{1-3}$alkyl group may bear one or two substituents selected from oxo, hydroxy, halogeno and $C_{1-3}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);

4) $C_{2-3}$alkyl$X^4C_{2-3}$alkyl$X^5R^{30}$ (wherein $X^4$ and $X^5$ are as defined hereinbefore) and $R^{30}$ represents hydrogen or $C_{1-2}$alkyl);

5) $C_{1-4}$alkyl$R^{70}$ (wherein $R^{70}$ is a group selected from pyrrolidinyl, piperazinyl, piperidinyl, 1,3-dioxolan-2-yl, 1,3-dioxan-2-yl, 1,3-dithiolan-2-yl and 1,3dithian-2-yl, which group is linked to $C_{1-4}$alkyl through a carbon atom and which group may carry one or two substituents selected from oxo, hydroxy, halogeno, $C_{1-2}$alkyl, $C_{1-2}$hydroxyalkyl and $C_{1-2}$alkoxy) or $C_{2-4}$alkyl$R^{71}$ (wherein $R^{71}$ is a group selected from morpholino, thiomorpholino, pyrrolidin-1-yl, piperazin-1-yl and piperidino which group may carry one or two substituents selected from oxo, hydroxy, halogeno, $C_{1-2}$alkyl, $C_{1-2}$hydroxyalkyl and $C_{1-2}$alkoxy); and 6) $(CH_2)_qX^6R^{37}$ (wherein $X^6$ is as defined hereinbefore; q is an integer from 1 to 3 if $X^6$ is a direct bond and q is 2 or 3 if $X^6$ is other than a direct bond; and $R^{37}$ is a phenyl group, a pyridone group or a 5 or 6 membered aromatic heterocyclic group with 1 to 2 heteroatoms selected from O, N and S, of which preferably one is N, which phenyl group, pyridone group or aromatic heterocyclic group may be substituted as hereinbefore defined, preferably substituted with one substituent selected from hydroxy, halogeno, $C_{1-2}$alkyl, $C_{1-2}$alkoxy, $C_{1-2}$hydroxyalkyl, $C_{1-2}$hydroxyalkoxy, carboxy, cyano, —CONR$^{43}$R$^{44}$ and —NR$^{45}$COR$^{46}$ (wherein $R^{43}$, $R^{44}$, $R^{45}$ and $R^{46}$, which may be the same or different, each represents hydrogen or $C_{1-2}$alkyl));

7) $C_{4-5}$alkenyl$R^{71}$ (wherein $R^{71}$ is as defined hereinbefore);

8) $C_{4-5}$alkynyl$R^{71}$ (wherein $R^{71}$ is as defined hereinbefore);

9) $C_{1-3}$alkyl$X^{10}C_{1-3}$alkyl$R^{37}$ (wherein $X^{10}$ and $R^{37}$ are as defined hereinbefore);

10) $R^{36}$ (wherein $R^{36}$ is as defined hereinbefore); and

11) $C_{1-3}$alkyl$X^{11}C_{1-3}$ alkyl$R^{36}$ (wherein $X^{11}$ and $R^{36}$ are as defined hereinbefore).

Preferably $R^{13}$ is selected from one of the following nine groups:

1) $C_{1-3}$alkyl which may be unsubstituted or substituted with one or more fluorine atoms, or $C_{2-3}$alkyl which may be unsubstituted or substituted with one or two groups selected from hydroxy and amino;

2) 2-(3,3-dimethylureido)ethyl, 3-(3,3-dimethylureido) propyl, 2-(3-methylureido)ethyl, 3-(3-methylureido) propyl, 2-ureidoethyl, 3-ureidopropyl 2(N,N-dimethylcarbamoyloxy)ethyl, 3-(N,N-dimethylcarbamoyloxy)propyl, 2-(N-methylcarbamoyloxy)ethyl, 3-(N-methylcarbamoyloxy) propyl, 2-(carbamoyloxy)ethyl, 3-(carbamoyloxy)propyl;

3) $C_{2-3}$alkyl$X^3R^{24}$ (wherein $X^3$ is as defined hereinbefore and $R^{24}$ is a group selected from $C_{1-2}$alkyl, cyclopentyl, cyclohexyl, pyrrolidinyl and piperidinyl which group is linked to $X^3$ through a carbon atom and which $C_{1-2}$alkyl group may bear one or two substituents selected from oxo, hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);

4) $C_{2-3}$alkyl$X^4C_{2-3}$alkyl$X^5R^{32}$ (wherein $X^4$ and $X^5$ are as defined hereinbefore) and $R^{30}$ represents hydrogen or $C_{1-2}$alkyl);

5) $C_{1-2}$alkyl$R^{70}$ (wherein $R^{70}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-2}$alkyl through a carbon atom and which group may carry one substituent selected from oxo, hydroxy, halogeno, $C_{1-2}$alkyl, $C_{1-2}$hydroxyalkyl and $C_{1-2}$alkoxy) or $C_{2-3}$alkyl$R^{59}$ (wherein $R^{59}$ is a group selected from morpholino, thiomorpholino, piperidino, piperazin-1-yl and pyrrolidin-1-yl which group may carry one or two substituents selected from oxo, hydroxy, halogeno, $C_{1-2}$alkyl, $C_{1-2}$hydroxyalkyl and $C_{1-2}$alkoxy);

6) $(CH_2)_qX^6R^{37}$ (wherein $X^6$ is as defined hereinbefore; q is an integer from 1 to 3 if $X^6$ is a direct bond and q is 2 or 3 if $X^6$ is other than a direct bond; and $R^{37}$ is a group selected from phenyl, a pyridone group, pyridyl, imidazolyl, thiazolyl, thienyl, triazolyl and pyridazinyl, preferably selected from phenyl, a pyridone group, pyridyl, imidazolyl, thiazolyl and triazolyl which group may be substituted with one substituent selected from hydroxy, halogeno, $C_{1-2}$alkyl, $C_{1-2}$alkoxy, $C_{1-2}$hydroxyalkyl, $C_{1-2}$hydroxyalkoxy, carboxy, cyano, —CONR$^{43}$R$^{44}$ and —NR$^{45}$COR$^{46}$ (wherein $R^{43}$, $R^{44}$, $R^{45}$ and $R^{46}$ are as defined hereinbefore);

7) $C_{1-3}$alkyl$X^{10}C_{1-3}$alkyl$R^{37}$ (wherein $X^{10}$ and $R^{37}$ are as defined hereinbefore);

8) $R^{36}$ (wherein $R^{36}$ is as defined hereinbefore); and

9) $C_{1-3}$alkyl$X^{11}C_{1-3}$alkyl$R^{36}$ (wherein $X^{11}$ and $R^{36}$ are as defined hereinbefore). More preferably $R^{13}$ represents 2-(methylthiazol-4-ylmethyl, 2-acetamidothiazol4-ylmethyl, 1-methylimidazol-2-ylmethyl, 4-pyridylmethyl, 2-(4-pyridyl)ethyl, 3-(4-pyridyl)propyl, 2-((N-(1-methylimidazol-4-ylsulphonyl)-N-methyl) amino)ethyl, 2-((N-(3-morpholinopropylsulphonyl)-N-methyl)amino)ethyl, 2-((N-methyl-N4-pyridyl)amino) ethyl, 2-(4-oxidomorpholino)ethyl, 3-(4-oxidomorpholino)propyl, 2-(4-oxo-1,4-dihydro-1-pyridyl)ethyl, 3-(4-oxo-1,4-dihydro-1-pyridyl)propyl, methyl, ethyl, trifluoromethyl, 2,2,2-trifluoroethyl, 2-hydroxyethyl, 3-hydroxypropyl, 2-(N,N-dimethylsulphamoyl)ethyl, 2(N-methylsulphamoyl)ethyl, (1,3-dioxolan-2-yl)methyl, 2-(1,3-dioxolan-2-yl)ethyl, 2-(2-methoxyethylamino)ethyl, 2-(2-hydroxyethylamino) ethyl, 3-(2-(2-methoxyethylamino)propyl, 3-(2-hydroxyethylamino)propyl, 2-(1,2,4-triazol-1yl)ethyl, 2-(1,2,4-triazol-4-yl)ethyl, 3-(1,2,4-triazol-1-yl)propyl, 3-(1,2,4-triazol-4-yl)propyl, 2-(4-pyridyloxy)ethyl, 3-(4-pyridyloxy)propyl, 2-(4-pyridylamino)ethyl, 3-(4-pyridylamino)propyl, 2-(2-methylimidazol-1-yl)ethyl, 3-(2-methylimidazol-1-yl)propyl, 2-(5-methyl-1,2,4-triazol-1-yl)ethyl, 3-(5-methyl-1,2,4-triazol-1-yl)propyl, morpholino, N-methylpiperazinyl, piperazinyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl) ethyl, 3-(piperazin-1-yl)propyl, 2-(pyrrolidin-1-yl)ethyl, 3-(pyrrolidin-1-yl)propyl, 2-methoxyethyl, 3-methoxypropyl, 2-(imidazol-1-yl)ethyl, 2-(1,2,3-triazol-1-yl)ethyl, 2-(1,2,3-triazol-2-yl)ethyl, 3-(imidazol-1-yl)propyl, 3-(1,2,3-triazol-1-yl)propyl, 3-(1,2,3-triazol-2-yl)propyl, 2-thiomorpholinoethyl, 3-thiomorpholinopropyl, 2-(1,1-dioxothiomorpholino) ethyl, 3-(1,1-dioxothiomorpholino)propyl, 2-(2-(oxyethoxy)ethyl, 2-(4-methylpiperazin-1-yl)ethyl, 3-(4-methylpiperazin-1-yl)propyl, 3-(methylsulphinyl)propyl, 3-(methylsulphonyl)propyl, 2-(methylsulphinyl)ethyl, benzyl, 2-sulphamoylethyl or 2-(methylsulphonyl)ethyl. Especially $R^{13}$ represents methyl, ethyl, trifluoromethyl, 2,2,2-trifluoroethyl, 2-hydroxyethyl, 3-hydroxypropyl, 2-methoxyethyl, 3-methoxypropyl, 2-(methylsulphinyl) ethyl, 2-(methylsulphonyl)ethyl, 2-(N,N- dimethylsulphamoyl)ethyl, 2-(N-methylsulphamoyl)ethyl, 2-sulphamoylethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, (1,3-dioxolan-2-yl)methyl, 2(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino)propyl, 2-(methylthiazol-4-ylmethyl, 2-acetamidothiazol-4-ylmethyl, 1-methylimidazol-2-ylmethyl, 2-(imidazol-1-yl)ethyl, 2-(1,2,3-triazol-1-yl)ethyl, 2-(1,2,3-triazol-2-yl)ethyl, 2-(1,2,4-triazol-1-yl)ethyl, 2 (1,2,4-triazol-4-yl)ethyl, 4-pyridylmethyl, 2-(4-pyridyl)ethyl, 3-(4-pyridyl)propyl, 3-(3-pyridyl)propyl, benzyl, 2-(4-pyridyloxy)ethyl, 2-(4-pyridylamino)ethyl, or 2-(4-oxo-1,4-dihydro-1-pyridyl)ethyl.

More especially $R^{13}$ represents methyl, ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(N,N-dimethylsulphamoyl)ethyl, 2-(N-methylsulphamoyl)ethyl, 2-sulphamoylethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino)propyl, 2-methylthiazol-4-ylmethyl, 2-acetamidothiazol4-ylmethyl, 1-methylimidazol-2-ylmethyl, 2-(imidazol-1-yl)ethyl, 2-(1,2,3-triazol-1-yl)ethyl, 2-(1,2,3-triazol-2-yl)ethyl, 2-(1,2,4-triazol-1yl)ethyl, 2-(1,2,4-triazol-4yl)ethyl, 4-pyridylmethyl, 2-(4-pyridyl)ethyl, 3-(4-pyridyl)propyl, benzyl, 2-(4-pyridyloxy)ethyl, 2-(4-pyridylamino)ethyl, or 2-(4-oxo-1,4-dihydro-1-pyridyl)ethyl.

In particular $R^1$ and $R^4$ are suitably hydrogen.

Examples of preferred groups for $R^2$ include $C_{1-6}$ alkoxy or cyano, and preferably $C_{1-6}$alkoxy such as methoxy.

The group $R^3$ is suitably selected from hydrogen or $C_{1-6}$alkoxy such as methoxy.

Preferably both $R^2$ and $R^3$ are $C_{1-6}$ alkoxy and are preferably methoxy.

Particular examples of compounds of formula (I) are listed in Table 1.

TABLE 1

| NO. | $R^1$ | $R^2$ | $R^3$ | $R^4$ | $R^5$ | $R^6$ | | Y | n | Mass spec | n.m.r. |
|---|---|---|---|---|---|---|---|---|---|---|---|
| 1 | H | OCH₃ | OCH₃ | H | Cl | | 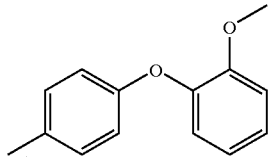 | NH | 0 | m/e 437 (M⁺ + H) | (d-6-DMSO, d values) 3.7(s, 3H), 3.75(s, 3H), 3.95(s, 3H), 6.85(m, 2H), 6.95(m, 1H), 7.05(m, 1H), 7.2(m, 4H), 7.45(s, 1H), 7.5(s, 1H), 8.8(s, 1H), 10.15(broad, 1H). |
| 2 | H | OCH₃ | OCH₃ | H | Br | | 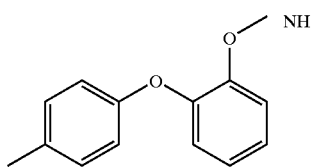 | NH | 0 | m/e 483 (M⁺ + H) | (d-6-DMSO, d values) 3.7(s, 3H), 3.75(s, 3H), 3.9(s, 3H), 6.85(m, 2H), 7.05(m, 2H), 7.2(m, 4H), 7.4(s, 1H), 7.45(s, 1H), 8.85(d, 1H), 10.0(b, 1H). |
| 3 | H | OCH₃ | OCH₃ | H | Cl | | 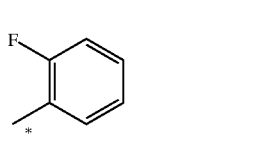 | NH | 0 | m/e 333 (M⁺ + H) | (d-6-DMSO, d values), 3.8(s, 3H), 3.95(s, 3H), 7.3(m, 3H), 7.4(m, 1H), 7.55(s, 1H), 7.75(s, 1H), 8.85(s, 1H), 10.22(broad, 1H). |
| 4 | H | OCH₃ | OCH₃ | H | Cl | | 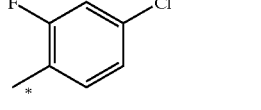 | NH | 0 | m/e 367 (M⁺ + H) | (d-6-DMSO, d values), 3.9(s, 3H), 3.95(s, 3H), 7.35(m, 2H), 7.55(s, 1H), 7.6(d, 1H), 7.85(s, 1H), 8.85(s, 1H), 10.3(broad, 1H). |
| 5 | H | OCH₃ | OCH₃ | H | Cl | | 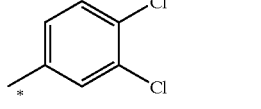 | NH | 0 | m/e 383 (M⁺ + H) | (d-6-DMSO, d values), 3.85(s, 3H), 3.95(s, 3H, 7.05(dd, 1H), 7.35(d, 1H), 7.5(s 1H), 7.55(d 1H), 7.75(s, 1H), 8.9(s, 1H), 10.32(broad, 1H). |
| 6 | H | OCH₃ | OCH₃ | H | Cl | | 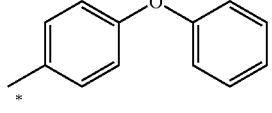 | NH | 0 | m/e 407 (M⁺ + H) | (d-6-DMSO, d values), 3.75(s, 3H), 3.95(s, 3H), 7.0(m, 4H), 7.1(m, 1H), 7.25(m, 2H), 7.4(m, 2H), 7.5(s, 1H), 7.6(s, 1H), 8.8(s, 1H), 10.3(broad, 1H). |

TABLE 1-continued

| NO. | R¹ | R² | R³ | R⁴ | R⁵ | R⁶ | Y | n | Mass spec | n.m.r. |
|---|---|---|---|---|---|---|---|---|---|---|
| 7 | H | OCH₃ | OCH₃ | H | Br | 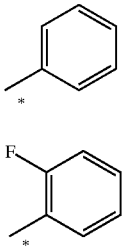 | NH | 0 | m/e 359 (M⁺ + H) | (d-6-DMSO, d values), 3.7(s, 3H), 3.9(s, 3H), 7.2(m, 3H), 7.4(m, 2), 7.48(s, 1H), 7.5(s, 1H), 8.9(s, 1H), 10.2(broad 1H). |
| 8 | H | OCH₃ | OCH₃ | H | Br | 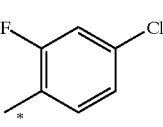 | NH | 0 | m/e 379 (M⁺ + H) | (d-6-DMSO, d values), 3.7(s, 3H), 3.9(s, 3H), 6.7(m, 1H), 7.0(m, 2H), 7.15(m, 1H), 7.35(s, 1H), 7.37(s, 1H), 8.35(broad, 1H), 8.6(s, 1H). |
| 9 | H | OCH₃ | OCH₃ | H | Br | 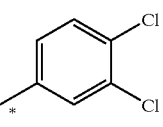 | NH | 0 | m/e 411 (M⁺ + H) | (d-6-DMSO, d values), 3.9(s, 3H), 3.95(s, 3H), 7.3(m, 2H), 7.5(s, 1H), 7.55(m, 1H), 7.825(s, 1H), 8.9(s, 1H), 10.1(broad, 1H). |
| 10 | H | OCH₃ | OCH₃ | H | Br | 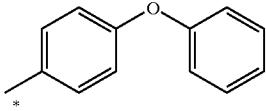 | NH | 0 | m/e 427 (M⁺ + H) | (d-6-DMSO, d values), 3.85(s, 3H), 3.95(s, 3H), 7.05(dd, 1H), 7.3(d, 1H), 7.5(s 1H), 7.55(d 1H), 7.75(s, 1H), 8.95(s, 1H), 10.26(broad, 1H). |
| 11 | H | OCH₃ | OCH₃ | H | Br | 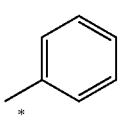 | NH | 0 | m/e 451 (M⁺ + H) | (d-6-DMSO, d values), 3.75(s, 3H), 3.95(s, 3H), 7.05(m, 4H), 7.15(m, 1H), 7.2(m, 2H), 7.4(m, 2H), 7.5(s, 1H), 7.55(s, 1H), 8.85(s, 1H), 10.0(broad, 1H). |
| 12 | H | CN | H | H | Cl | 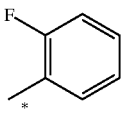 | NH | 0 | m/e 280 (M⁺ + H) | (d-6-DMSO, d values) 7.15(m, 3H), 7.35(m, 2H), 8.15(m, 1H), 8.25(d, 1H), 8.9(s, 1H), 8.95(s, 1H), 10.35(broad, 1H). |
| 13 | H | CN | H | H | Cl | 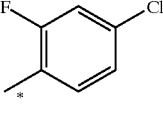 | NH | 0 | m/e 298 (M⁺ + H) | (d-6-DMSO, d values), 7.1(m, 3H), 7.25(m, 1H), 8.02(m, 1H), 8.1(m, 1H), 8.75(s, 1H), 8.85(d, 1H), 9.1(broad, 1H). |
| 14 | H | CN | H | H | Cl | 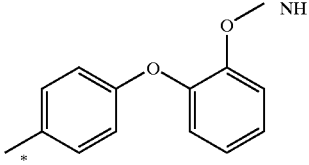 | NH | 0 | m/e 332 (M⁺ + H) | (d-6-DMSO, d values), 7.2(m, 2H), 7.5(m, 1H), 8.15(m, 2H), 8.9(s, 1H), 9.0(s, 1H). |
| 15 | H | CN | H | H | Cl | 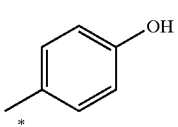 | NH | 0 | m/e 402 (M⁺ + H) | (d-6-DMSO, d values), 3.7(s, 3H), 6.8(m, 2H), 6.9(m, 4H), 7.15(m, 2H), 7.95(m, 1H), 8.05(m, 1H), 8.65(d, 1H), 8.75(s, 1H), 9.05(broad, 1H). |
| 16 | H | CN | H | H | Cl | 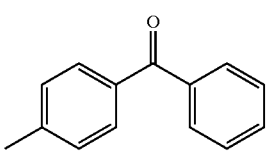 | NH | 0 | m/e 296 (M⁺ + H) | (d-6-DMSO, d values), 6.8(d, 2H), 7.05(d, 2H), 8.1(dd, 1H), 8.2(d, 1H), 8.75(s, 1H), 8.9(s, 1H), 10.33(broad, 1H). |
| 17 | H | CN | H | H | Cl |  | NH | 0 | m/e 384 (M⁺ + H) | (d-6-DMSO, d values), 7.0(d, 2H), 7.5(m, 2H). 7.6(m, 1H), 7.7(m, 4H), 8.1(dd, 1H), 8.2(d, 1H), 8.8(d, 1H), 9.0(s, 1H), 10.02(broad, 1H). |

TABLE 1-continued

| NO. | R¹ | R² | R³ | R⁴ | R⁵ | R⁶ | Y | n | Mass spec | n.m.r. |
|---|---|---|---|---|---|---|---|---|---|---|
| 18 | H | CN | H | H | Br | 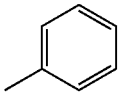 | NH | 0 | m/e 324/326 (M⁺ + H) | (d-6-DMSO, d values) 7.15(m, 3H), 7.35(m, 2H), 8.2(m, 2H), 8.8(s, 1H), 9.05(s, 1H), 10.1(broad, 1H). |
| 19 | H | CN | H | H | Br | 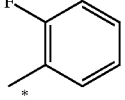 | NH | 0 | m/e 342 (M⁺ + H) | (d-6-DMSO, d values), 7.0(m, 1H), 7.1(m, 2H), 7.2(m, 1H), 8.05(dd, 1H), 8.1(d, 1H), 8.8(d, 1H), 8.9(s, 1H), 9.0(broad, 1H). |
| 20 | H | CN | H | H | Br | 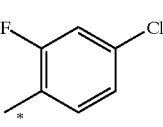 | NH | 0 | m/e 376 (M⁺ + H) | (d-6-DMSO, d values), 7.15(t, 1H), 7.25(dd, 1H), 7.5(dd, 1H), 8.2(s, 2H), 9.05(s, 1H), 9.1(s, 1H). |
| 21 | H | CN | H | H | Br | 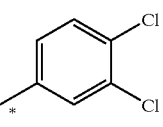 | NH | 0 | m/e 392 (M⁺ + H) | (d-6-DMSO, d values), 6.9(dd, 1H), 7.15(d, 1H), 7.5(d, 1H), 8.1(dd, 1H), 8.15(d, 1H), 8.85(d, 1H), 9.05(s, 1H), 9.85(broad, 1H). |
| 22 | H | CN | H | H | Cl | 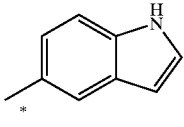 | NH | 0 | m/e 319 (M⁺ + H) | (d-6-DMSO, d values), 6.45(m, 1H), 7.0(dd, 1H), 7.4(m, 3H), 8.15(dd, 1H), 8.2(d, 1H), 8.65(s, 1H), 8.95(s, 1H), 10.6(broad, 1H), 11.35(broad, 1H). |
| 23 | H | CN | H | H | Cl | 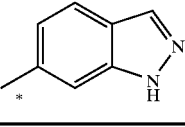 | NH | 0 | m/e 320 (M⁺ + H) | (d-6-DMSO, d values), 6.8(m, 2H), 7.6(d, 1H), 7.95(s, 1H), 8.02(dd, 1H), 8.15(d, 1H), 8.7(d, 1H), 8.85(s, 1H), 9.25(broad, 1H), 12.7(broad, 1H). | where * indicates the point of attachment.

Certain compounds of formula (I) are novel and these provide a further aspect of the invention. In particular, the invention provides a compound of formula (IA) which comprises a compound of formula (I), provided that where R⁵ is bromo, R⁶ is other than phenyl, methyl substituted phenyl or di-halo substituted phenyl.

Thus Examples of compounds of formula (IA) are compounds of formula (I) where R⁵ is chloro.

Other compounds of formula (IA) are compounds of formula (I) where R⁵ is bromo and R⁶ is cycloalkyl of 3 to 7 carbon atoms, which may be optionally substituted with one or more alkyl of 1 to 6 carbon atom groups; or is a pyridinyl pyrimidinyl, ring; wherein the pyridinyl, pyrimidinyl, or phenyl ring may be substituted with one, two or three groups selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenyl, benzoyl, amino, alkylamino of 1–6 carbon atoms, dialkylamino of 2 to 12 carbon atoms, alkanoylamino of 1–6 carbon atoms, alkenoylamino of 3–8 carbon atoms, alkynoylamino of 3–8 carbon atoms, and benzoylamino; or two adjacent substitutents on said, pyridyl or pyrimidinyl ring may be joined together to form a fused ring, which ring may be aromatic or non-aromatic in character and which may contain further heteroatoms, or R⁶ is a group —R⁵—X—R⁹ where R⁸, X and R⁹ are as defined above.

Yet further compounds of formula (IA) are compounds of formula (I) where R⁶ is phenyl which is substituted with one, two or three groups selected from the group consisting of alkyl of 2–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenyl, benzoyl, amino, alkylamino of 1–6 carbon atoms, dialkylamino of 2 to 12 carbon atoms, alkanoylamino of 1–6 carbon atoms, alkenoylamino of 3–8 carbon atoms, alkynoylamino of 3–8 carbon atoms, and benzoylamino; or two adjacent substitutents on said phenyl ring may be joined together to form a fused ring, which ring may be aromatic or non-aromatic in character and which may contain further heteroatoms Preferred classes of compound of formula (IA) include those listed above in respect of formula (I).

Compounds of formula (I) are suitably prepared by reacting a compound of formula (III)

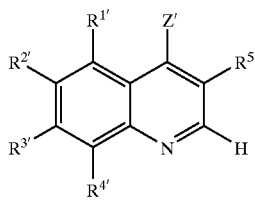

(III)

where $R^{1'}$, $R^{2'}$, $R^{3'}$, $R^{4'}$ represent $R^1$, $R^2$, $R^3$ and $R^4$ respectively as defined in relation to formula (I) or a precursor thereof, $R^5$ is as defined in relation to formula (I), and $Z'$ is a leaving group, with a compound of formula (IV)

where Y, X, and n are as defined in relation to formula (I), and $R^{6'}$ is a group $R^6$ as defined in relation to formula (I) or a precursor thereof; and thereafter if necessary or desired converting precursor groups $R^{1'}$, $R^{2'}$, $R^{3'}$, $R^{4'}$ and $R^{6'}$ to groups of formula $R^1$, $R^2$, $R^3$, $R^4$ and $R^6$ respectively, or converting a group $R^1$, $R^2$, $R^3$, $R^4$ and $R^6$ to a different such group.

Suitable leaving groups for $Z'$ include halogen such as bromo or chloro, or a mesylate or tosylate group. In particular $Z'$ is chloro.

The reaction is suitably carried out in an organic solvent such as an alcohol for example propanol, cyclohexanol, at elevated temperatures, for example of from 50 to 150° C., for example at about 105° C. or 110° C.

Conversion reactions in which precursor groups $R^{1'}$, $R^{2'}$, $R^{3'}$, $R^{4'}$ are converted to groups of formula $R^1$, $R^2$, $R^3$ and $R^4$ respectively, or groups $R^1$, $R^2$, $R^3$ and $R^4$ are converted to different such group can be carried out using conventional chemistry as described in the literature. Particular precursor groups $R^{1'}$, $R^{2'}$, $R^{3'}$, $R^{4'}$ are groups of formula $R^{13'}$—$X^1$—$(CH_2)_x$ wherein x and $X^1$ are as defined hereinafter, and $R^{13'}$ is $C_{1-5}$alkyl which is substituted with halo other than fluoro, and in particular chloro or bromo. The chloro group may readily be converted many other groups $R^{13}$ as defined in relation to claim 1. Such compounds are novel and form a further aspect of the invention. They may have activity similar to that of compounds of formula (I) in their own right and therefore may be used in place of a compound of formula (I).

Thus the invention further provides a compound of formula (IB)

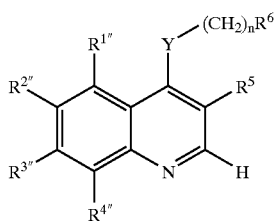

(IB)

where Y, n, $R^5$ and $R^6$ are as defined above and at least one of $R^{1''}$, $R^{2''}$, $R^{3''}$ or $R^{4''}$ is a group $R^{13'}$—$X^1$—$(CH_2)_x$ wherein $X^7$ and x are as above and $R^{13'}$ is alkyl substituted by chloro or bromo; and the remainder are groups $R^1$, $R^2$, $R^3$ and $R^4$ respectively.

Similarly conversion reactions involving groups $R^{6'}$ may be effected using conventional chemistry. For example substitutent groups on a group $R^6$ may be changed, for example by changing acids to esters or amides etc.

A further example, to produce compounds of formula (I) where $R^6$ is a group —$R^8$—X—$R^9$ it to react a compound of formula (V)

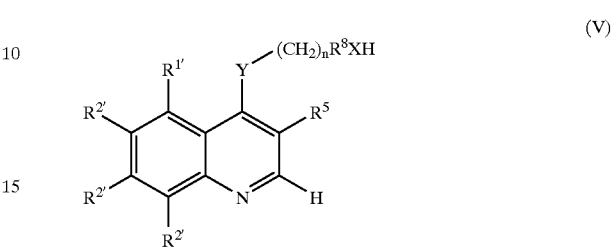

(V)

where $R^{1'}$, $R^{2'}$, $R^{3'}$, $R^{4'}$ are as defined in relation to formula (III) $R^8$, X, Y and n are as defined in relation to formula (I), with a compound of formula (VI)

where $R^{9'}$ is a group $R^9$ as defined in relation to formula (IV) or a precursor thereof and $Z''$ is a leaving group;

and thereafter if necessary or desired converting precursor groups $R^{1'}$, $R^{2'}$, $R^{3'}$, $R^{4'}$ and $R^{9'}$ to groups of formula $R^1$, $R^2$, $R^3$, $R^4$ and $R^9$ respectively, or converting a group $R^1$, $R^2$, $R^3$, $R^4$ and $R^9$ to a different such group. Suitable leaving groups for $Z''$ include halogen such a bromo or chloro, or a mesylate or tosylate group. Conversion reactions are as described above.

The reaction is suitably carried out in an organic solvent such as DMF at elevated temperatures, for example of from 40 to 120° C., for example at about 80° C.

Preferably however, $R^{1'}$, $R^{2'}$, $R^{3'}$, $R^{4'}$, and $R^{6'}$ are groups $R^1$, $R^2$, $R^3$, $R^4$ and $R^6$ respectively and so no subsequent processing is required.

Certain compounds of formula (III) are disclosed in WO98/13350 and others can be prepared from known compounds by analogous methods. For example, they are suitably prepared by reacting a compound of formula (V)

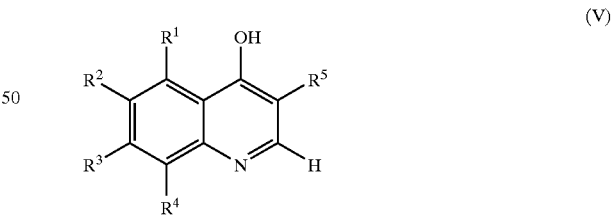

(V)

where $R^1$, $R^2$, $R^3$, $R^4$ and $R^5$ are as defined in relation to formula (I), with a compound of formula (VI)

where $Z'$ is as defined above and $R^{20}$ is a further leaving group such as sulphonylchloride. A particular example of a compound of formula (VI) is thionyl chloride.

The reaction is suitably effected in an organic solvent such as dimethylformamide, at elevated temperatures for example of from 50 to 150° C., and conveniently at the reflux temperature of the solvent.

Compounds of formula (V) may be prepared by chlorination or bromination of a compound of formula (VII)

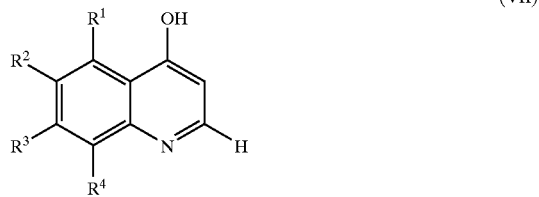

(VII)

where $R^1$, $R^2$, $R^3$ and $R^4$ are as defined in relation to formula (I).

Halogenation can be effected using known halogenating agents such as N-halosuccinimides. The reaction is suitably effected in an organic solvent such as carbon tetrachloride. It may advantageously be carried out in the presence of a radical initiator such as azobisisobutyronitrile. Elevated temperatures of from 40 to 76° C. are suitably employed. Where $R^5$ is bromine, the reaction can also be effected using bromine in aqueous solution in the presence of a base such as sodium hydroxide. A suitable temperature for such a reaction would be in the range of from 20 to 25° C.

Compounds of formula (VII) are either known compounds (see for example WO99/00372 and WO9847873, or they can be prepared from known compounds by conventional methods. Compounds of formula (IV) are also either known compounds (see for example Rev. Chim. (Bucharest (1988), 39(6), 477–82, DD110651:74.01.05) or they can be prepared from known compounds by conventional methods.

Compounds of the invention are useful in the inhibition of MEK enzyme activity and can be used in the treatment of proliferative disease. They will suitably be in the form of a pharmaceutical composition, in combination with a pharmaceutically acceptable carrier. Such compositions form a further aspect of the invention.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid.

Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, and esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30μ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent to compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine. As mentioned above, compounds of the Formula I are useful in treating diseases or medical conditions which are due alone or in part to the effects of MEK enzymes.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

In a further aspect, the invention provides a method of treating proliferative disease by administering a compound of formula (I) as described above, or a pharmaceutical composition as described above.

Yet a further aspect of the invention provides the use of a compound of formula (I) as defined above, in the preparation of a medicament for use in the inhibition of MEK enzyme activity and in particular for the treatment of proliferative disease such as cancer.

The invention will now be particularly described by way of Example.

EXAMPLE 1

Preparation of Compound 1 in Table 1

Step 1

N-chlorosuccinimide (1.8 g) and azobisisobutyronitrile (0.1 g) were added to a suspension of 6,7-dimethoxy-4-quinolone (2.05 g) in carbon tetrachloride (100 ml). The mixture was stirred and heated to reflux for 6 hours. The mixture was filtered. The solid was washed with water and then dried. There was thus obtained 3-chloro-6,7-dimethoxy-4-quinolone (1.6 g, 66%).

Mass Spectrum m/e 240 ($M^+$+H).

NMR Spectrum (d-6-DMSO, d values) 3.85 (s, 6H), 7.0 (s, 1H), 7.4 (s, 1H), 8.2 (d, 1H).

Step 2

A mixture of the product of step 1 (1.6 g), thionyl chloride (25 ml) and DMF (3 drops) was stirred and heated to reflux for 5 hours. The thionyl chloride was evaporated. The residue was treated with toluene which was then evaporated. This procedure was repeated. The residue was then triturated with diethyl ether and then filtered. There was thus obtained 3,4-dichloro-6,7-dimethoxyquinoline (1.65 g, 95%).

NMR Spectrum ($CDCl_3$, d values) 4.15 (s, 3H), 4.2 (s, 3H), 7.5 (s, 1H), 8.2 (s, 1H), 8.8 (s, 1H).

Step 3

A mixture of 3,4-dichloro-6,7-dimethoxyquinoline (258 mg) and 4-(2-(oxyphenoxy)-aniline (243 mg) in 1-propanol (15 ml) was stirred and heated at 100° C. for 18 hours. The mixture was cooled to ambient temperature and then filtered. The crystals were washed with a small volume of 1-propanol and then dried to give 4-(2-methoxyphenoxy)-anilino-3-chloro-6,7-dimethoxyquinoline (Compound 1 in Table 1) (243 mg, 51%).

EXAMPLE 2

By an analogous procedure to that described in Example 1 but using an alternative aniline, the following compounds were prepared.

Compound No 3 in Table 1—(from 2-fluoroaniline),
Compound No 4 in Table 1—(from 4-chloro-2-fluoro-aniline),
Compound No 5 in Table 1—(from 3,4-dichloroaniline),
Compound No 6 in Table 1—(from 4-phenoxyaniline).

EXAMPLE 3
Preparation of Compound 2 in Table 1
Step 1

N-bromosuccinimide (4.9 g) and azobisisobutyronitrile (0.2 g) were added to a suspension of 6,7-dimethoxy-4-quinolone (4.1 g) in carbon tetrachloride (200 ml). The mixture was stirred and heated to reflux for 6 hours. The mixture was filtered. The solid was suspended in water and then filtered and then dried. There was thus obtained 3-bromo-6,7-dimethoxy-4-quinolone (3.2 g, 56%).

Mass Spectrum m/e 284/286 ($M^+$+H).

NMR Spectrum (d-6-DMSO, d values) 3.8 (s, 3H), 3.85 (s, 3H), 7.0 (s, 1H), 7.4 (s, 1H), 8.2 (d, 1H)
Step 2

A mixture of the product obtained in Step 1 (3.2 g), thionyl chloride (50 ml) and DMF (5 drops) was stirred and heated to reflux for 2 hours. The thionyl chloride was evaporated. The residue was treated with toluene which was then evaporated. This procedure was repeated. There was thus obtained crude 3-bromo-4-chloro-6,7-dimethoxyquinoline (3.8 g,).

NMR Spectrum (d-6-DMSO, d values) 3.9 (s, 6H), 7.4 (s, 1H), 7.45 (s, 1H), 8.8 (s, 1H).
Step 3

A mixture of 3-bromo-4-chloro-6,7-dimethoxyquinoline (302 mg) and 4-(2-methoxyphenoxy)-aniline (236 mg) in cyclohexanol (5 ml) was stirred and heated at 130° C. for 24 hours. The mixture was cooled to ambient temperature and then filtered. The crystals were washed first with methanol and then with diethyl ether and then dried to give 4-(2-methoxyphenoxy)-anilino-3-bromo-6,7-dimethoxyquinoline (Compound 2) (180 mg, 37%).

EXAMPLE 4

By an analogous procedure to that described for Example 3 but using an alternative aniline, the following compounds were prepared. Compound No. 7 in Table 1—(from aniline), Compound No. 8 in Table 1—(from 2-fluoroaniline), Compound No. 9 in Table 1—(from 4-chloro-2-fluoro-aniline), Compound No. 10 in Table 1—(from 3,4-dichloroaniline), Compound No. 11 in Table 1 —(from 4-phenoxyaniline).

EXAMPLE 5
Preparation of Compound No 12 in Table 1
Step 1

Sodium hypochlorite solution (10% chlorine, 7.5 ml) was added dropwise to a suspension of 6-cyano-4-quinolone (1.7 g) in sodium hydroxide solution (2 molar, 15 ml). The mixture was stirred and cooled in ice to keep the temperature <25° C. The mixture was left to stand for 18 hours and then a further quantity of sodium hypochlorite solution (10% chlorine, 3 ml) was added dropwise. Water (25 ml) was added to the mixture. The mixture was filtered and the filtrate acidified with acetic acid. The solid which precipitated was collected by filtration and washed with water. There was thus obtained 3-chloro-6-cyano-4-quinolone (1.25 g, 61%).

Mass Spectrum m/e 205 ($M^+$+H).

NMR Spectrum (d-6-DMSO, d values) 7.7 (d, 1H), 8.0 (m, 1H), 8.5 (m, 2H).
Step 2

A mixture of the product obtained in Step 1 (1.2 g), thionyl chloride (20 ml) and DMF (2 drops) was stirred and heated to reflux for 18 hours. The thionyl chloride was evaporated. The residue was treated with toluene which was then evaporated. There was thus obtained crude 3,4-dichloro-6-cyanoquinoline (1.3 g).

NMR Spectrum (d-6-DMSO, d values) 8.15 (m, 1H), 8.25 (d, 1H), 8.75 (m, 1H), 9.15 (s, 1H).
Step 3

A mixture of 3,4-dichloro-6-cyanoquinoline (230 mg) and aniline (112 mg) in 1-propanol (5 ml) was stirred and heated at 100° C. for 24 hours. The mixture was cooled to ambient temperature. The product crystallised from the solution and was collected by filtration and washed with 1-propanol. There was thus obtained 4-anilino-3-chloro-6-cyanoquinoline (102 mg, 36%)

EXAMPLE 6

By an analogous procedure to that described for Example 5 but using an alternative aniline, the following compounds were prepared:
Compound No 13 in Table 1—(from 2-fluoroaniline),
Compound No 14 in Table 1 (from 4-chloro-2-fluoro-aniline),
Compound No 15 in Table 1(from 4-(2-(oxyphenoxy)-aniline).
Compound No 16 in Table 1 (from 4-hydroxyaniline),
Compound No. 17 in Table 1 (from 4-benzoylaniline).
Compound No. 22 in Table 1 (from 5-aminoindole),
Compound No 23 in Table 1 (from 6-aminoindazole).

EXAMPLE 7
Preparation of Compound No 18 in Table 1
Step 1

A solution of bromine was prepared by dissolving bromine (16 g) in water (100 ml) containing potassium bromide (30 g). This solution containing bromine (54 ml) was added dropwise to a suspension of 6-cyano-4-quinolone (5.1 g) in sodium hydroxide solution (2 molar, 60 ml). The mixture was stirred and cooled in ice to keep the temperature at about 20° C. The mixture was left to stir for 4 hours and then a further quantity of the bromine solution (15 ml) was added dropwise with the temperature kept below 25° C. The mixture was stirred for a further 1 hour and was then filtered. There was thus obtained 3-bromo-6-cyano-4-quinolone (5.85 g, 78%).

Mass Spectrum m/e 249/251 ($M^+$+H).

NMR Spectrum (d-6-DMSO, d values) 7.7 (d, 1H), 7.95 (m, 1H), 8.45 (d, 1H), 8.55 (s, 1H).
Step 2

A mixture of the product of step 1 (5.8 g), thionyl chloride (100 ml) and DMF (10 drops) was stirred and heated at 90° C. for 18 hours. The thionyl chloride was evaporated. The residue was treated with toluene which was then evaporated. There was thus obtained crude 3-bromo-4-chloro-6-cyanoquinoline (6.58 g).

NMR Spectrum (d-6-DMSO, d values) 8.2 (d, 1H), 8.25 (s, 1H), 8.75 (s, 1H), 9.2 (s, 1H).
Step 3

A mixture of 3-bromo-4-chloro-6-cyanoquinoline (267 mg) and aniline (186 mg) in 1,4-dioxane (15 ml) was stirred and heated in a heater at 120° C. for 22 hours. The mixture was cooled to ambient temperature. The 1,4-dioxane was evaporated. The residue was treated with dichloromethane (5 ml) tetramethyl guanidine (0.125 ml) and then purified by column chromatography using initially dichloromethane then methanol/dichloromethane mixtures as eluent. The product was dissolved in ethanol. The solution was acidified to pH 1–2 by addition of a solution of hydrogen chloride in diethyl ether (1.0 molar) and the product isolated by filtration. There was thus obtained 4-anilino-3-bromo-6-cyanoquinoline(104 mg, 28%).

EXAMPLE 8

By an analogous procedure to that described for example 7 but using an alternative aniline, the following compounds were prepared.

Compound 19 in Table 1 (from 2-fluoroaniline),
Compound 20 in Table 1 (from 4-chloro-2-fluoro-aniline),
Compound 21 in Table 1 (from 3,4-dichloroaniline), Biological Results Assay for Inhibitors of the MAP Kinase Pathway To evaluate inhibitors of the MAPK pathway a coupled assay was carried out which measures phosphorylation of serine/threonine residues present in the substrate in the presence or absence of inhibitor. Recombinant glutathione S-transferase fusion protein containing human p45MEK1 (GST-MEK) was activated by c-raf (Sf9 insect cell lysate from triple baculoviral infection with c-raf/ras/lck) and used for the assay. Active GST-MEK was first used to activate a recombinant glutathione S-transferase fusion protein containing p44MAP kinase (GST-MAPK) in the presence of ATP and $Mg^{2+}$ for 60min at room temperature in the presence or absence of potential inhibitors. The activated GST-MAPK was then incubated with myelin basic protein (MBP) as substrate for 10 min at room temperature in the presence of ATP, $Mg^{2+}$ and $^{33}$P-ATP. The reaction was stopped by addition of 20% v/v phosphoric acid. Incorporation of $^{33}$P into the myelin basic protein was determined by capture of the substrate on a filter mat, washing and counting using scintillation methods. The extent of inhibition was determined by comparison with untreated controls.

The final assay solution contained 10 mM Tris, pH 7.5, 0.05 mM EGTA, 8.33 $\mu$M [$\gamma^{33}$P]ATP, 8.33 mM $Mg(OAc)_2$, 0.5 mM sodium orthovanadate, 0.05% w/v BSA, 6.5 ng GST-MEK, 1 $\mu$g GST-MAPK and 16.5 $\mu$g MBP in a reaction volume of 60 $\beta$l.

Compounds tested of the present invention had $IC_{50}$ results typically less than 20 $\mu$M. For example, Compound no 5 of Example 2 gave an $IC_{50}$ of 1.53 $\mu$M.

In vitro MAP Kinase Assay

To determine whether compounds were inhibiting GST-MEK or GST-MAPK, a direct assay of MAPK activity was employed. GST-MAPK was activated by a constitutively active GST-MEK fusion protein containing two point mutations (S217E, S221E) and used for the assay in the presence and absence of potential inhibitors. The activated GST-MAPK was incubated with substrate (MBP) for 60 min at room temperature in the presence of ATP, $Mg^{2+}$ and $^{33}$P-ATP. The reaction was stopped by addition of 20% v/v phosphoric acid. Incorporation of $^{33}$P into the myelin basic protein was determined by capture of the substrate on a filter mat, washing and counting using scintillation methods.

The final assay solution contained 12 mM Tris, pH 7.5, 0.06 mM EGTA, 30 $\mu$M [$\gamma^{33}$P]ATP, 10 mM $Mg(OAc)_2$, 0.6 mM sodium orthovanadate, 0.06% w/v BSA, 28 ng GST-MAPK and 16.5 $\mu$g MBP in a reaction volume of 60 $\mu$l.

Compounds of the invention showed activity in this screen.

Cell Proliferation Assays

Cells were seeded into multi-well plates at 20 000–40 000 cells/ml in growth medium containing 5% FCS and incubated overnight at 37° C. The compounds were prepared in fresh medium at an appropriate concentration and added to the wells containing the cells. These were then incubated for a further 72 hours. Cells were then either removed from the wells by incubating with trypsin/EDTA and counted using a Coulter counter, or treated with KIT/PMS in PBSA and optical densities read at 45 nM. Compounds tested of the present invention had $IC_{50}$ results typically less than 30 $\mu$M. Compound No 1 of Example 1 gave an IC50 of 3.4 $\mu$M in HT29 human colon tumour cells.

What is claimed is:

1. A compound of formula (I)

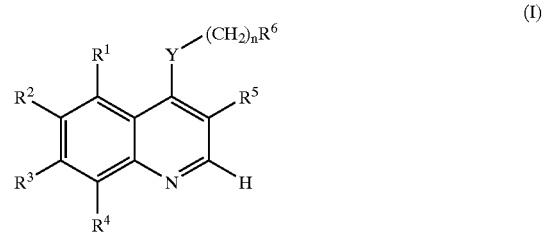

or a pharmaceutically acceptable salt thereof; wherein:

n is 0–1;

Y is —NH—;

$R^5$ is chloro or bromo;

$R^6$ is cycloalkyl of 3 to 7 carbon atoms, which may be optionally substituted with one or more alkyl of 1 to 6 carbon atom groups; or is a pyridinyl, pyrimidinyl, or phenyl ring; wherein the pyridinyl, pyrimidinyl, or phenyl ring may be substituted with one, two or three groups selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenyl, benzoyl, amino, alkylamino of 1–6 carbon atoms, dialkylamino of 2 to 12 carbon atoms, alkanoylamino of 1–6 carbon atoms, alkenoylamino of 3–8 carbon atoms, alkynoylamino of 3–8 carbon atoms, and benzoylamino; or two adjacent substitutents on said phenyl, pyridyl or pyrimidinyl ring may be joined together as a 5-membered heterocyclic ring having one or two nitrogen atoms, to form a fused ring;

or $R^6$ is a group —$R^8$—X—$R^9$ where $R^8$ is a divalent cycloalkyl of 3 to 7 carbon atoms, which may be optionally further substituted with one or more alkyl of 1 to 6 carbon atom groups; or is a divalent pyridinyl, pyimidinyl, or phenyl ring; wherein the pyridinyl, pyrimidinyl, or phenyl ring may be optionally further substituted with one or more groups selected from halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino;

where X is selected from $CH_2$, —NH—, —O—, —S—, $CH_2$ or —$NR^5$— where $R^5$ is alkyl of 1–6 carbon atoms, and $R^9$ is a group $(CH_2)_m R^{10}$ where m is 0, or an integer of from 1–3 and $R^{10}$ is an optionally substituted aryl or optionally substituted cycloalkyl ring of up to 10 carbon atoms, or $R^{10}$ is a heterocyclic ring containing 1 or 2 oxygen atoms and optionally one or more substituents;

$R^1$, $R^2$, $R^3$ and $R^4$ are each independently selected from hydrogen, hydroxy, halogeno, cyano, nitro, trifluoromethyl, $C_{1-3}$alkyl, —$NR^{11}R^{12}$ (wherein $R^{11}$ $R^{12}$, which may be the same or different, each represents hydrogen or $C_{1-3}$alkyl), or a group $R^{13}$—$X^1$—$(CH_2)_x$ wherein x is 0 to 3, $X^1$ represents —O—, —$CH_2$—, —OCO—, carbonyl, —S—, —SO—, —$SO_2$—, —$NR^{14}CO$—, —$CONR^{15}$—, —$SO_2NR^{16}$—, —$NR^{17}SO_2$— or —$NR^{18}$— (wherein $R^{14}$, $R^{15}$, $R^{16}$, $R^{17}$ and $R^{18}$ each independently represents hydrogen, $C_{1-3}$alkyl or $C_{1-3}$alkoxy$C_{2-3}$alkyl) and $R^{13}$ is selected from one of the following sixteen groups:

1) $C_{1-5}$alkyl which may be unsubstituted or which may be substituted with one or more groups selected from hydroxy, fluoro and amino;

2) $C_{1-5}$alkyl$X^2COR^{19}$ (wherein $X^2$ represents —O— or $NR^{20}$— (wherein $R^{20}$ represents hydrogen, $C_{1-3}$alkyl or $C_{1-3}$alkoxy$C_{2-3}$alkyl) and $R^{19}$ represents —$NR^{21}R^{22}$— or —$OR^{23}$— (wherein $R^{21}$, $R^{22}$ and $R^{23}$ which may be the same or different each represents hydrogen, $C_{1-3}$alkyl or $C_{1-3}$alkoxy$C_{2-3}$alkyl));

3) $C_{1-5}$alkyl$X^3R^{24}$ (wherein $X^3$ represents —O—, —S—, —SOH—, —$SO_2$—, —OCO—, —$NR^{25}CO$—, —$CONR^{26}$—, —$SO_2NR^{27}$—, —$NR^{28}SO_2$— or —$NR^{29}$— (wherein $R^{25}$, $R^{26}$, $R^{27}$, $R^{28}$ and $R^{29}$ each independently represents hydrogen, $C_{1-3}$alkyl or $C_{1-3}$alkoxy$C_{2-3}$alkyl) and $R^{24}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-4}$alkoxy and which cyclic group may bear one or two substituents selected from oxo, hydroxy, halogeno, $C_{1-4}$alkyl, $C_{1-4}$hydroxyalkyl and $C_{1-4}$alkoxy);

4) $C_{1-5}$alkyl$X^4C_{1-5}$alkyl$X^5R^{30}$ (wherein $X^4$ and $X^5$ which may be the same or different are each —O—, —S—, —SO—, —$SO_2$—, —$NR^{31}CO$—, —$CONR^{32}$—, —$SO_2NR^{33}$—, —$NR^{34}SO_2$— or —$NR^{35}$— (wherein $R^{31}$, $R^{32}$, $R^{33}$, $R^{34}$ and $R^{35}$ each independently represents hydrogen, $C_{1-3}$alkyl or $C_{1-3}$alkoxy$C_{2-3}$alkyl) and $R^{30}$ represents hydrogen or $C_{1-3}$alkyl);

5) $C_{1-5}$alkyl$R^{36}$ (wherein $R^{36}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy);

6) $(CH_2)_q X^6 R^{37}$ (wherein q is an integer from 0 to 5, $X^6$ represents a direct bond, —O—, —S—, —SO—, —$SO_2$—, —$NR^{38}CO$—, —$CONR^{39}$—, —$SO_2NR^{40}$—, —$NR^{41}SO_2$— or —$NR^{42}$— (wherein $R^{38}$, $R^{39}$, $R^{40}$, $R^{41}$ and $R^{42}$ each independently represents hydrogen, $C_{1-3}$alkyl or $C_{1-3}$alkoxy$C_{2-3}$alkyl) and $R^{37}$ is a phenyl group, a pyridone group or a 5 or 6 membered aromatic heterocyclic group with 1 to 3 heteroatoms selected from O, N and S, which phenyl, pyridone or aromatic heterocyclic group may carry up to 5 substituents selected from hydroxy, halogeno, amino, $C_{1-4}$alkyl, $C_{1-4}$alkoxy, $C_{1-4}$hydroxyalkyl, $C_{1-4}$hydroxyalkoxy, $C_{1-4}$aminoalkyl, $C_{1-4}$alkylamino, carboxy, cyano, —$CONR^{43}R^{44}$ and —$NR^{45}COR^{46}$ (wherein $R^{43}$, $R^{44}$, $R^{45}$ and $R^{46}$, which may be the same or different, each represents hydrogen, $C_{1-4}$alkyl or $C_{1-3}$alkoxy$C_{2-3}$alkyl));

7) $C_{2-6}$alkenyl$R^{36}$ (wherein $R^{36}$ is as defined hereinbefore);

8) $C_{2-6}$alkynyl$R^{36}$ (wherein $R^{36}$ is as defined hereinbefore);

9) $X^7R^{47}$ (wherein $X^7$ is —$SO_2$—, —O— or —$CONR^{48}R^{49}$— (wherein $R^{48}$ and $R^{49}$, which may be the same or different, each represents hydrogen, $C_{1-3}$alkyl or $C_{1-3}$alkoxy$C_{2-3}$alkyl) and $R^{47}$ represents $C_{1-5}$alkyl which may be unsubstituted or which may be substituted with one or more groups selected from hydroxy, fluoro and amino) with the provisos that when $X^7$ is —$SO_2$—, $X^1$ is —O—, when $X^7$ is —O—, $X^1$ is carbonyl, when $X^7$ is —$CONR^{48}R^{49}$—, $X^1$ is —O— or $NR^{18}$ (wherein $R^{48}$, $R^{49}$ and $R^{18}$ are as defined hereinbefore);

10) $C_{2-6}$alkenyl$R^{37}$ (wherein $R^{37}$ is as defined hereinbefore);

11) $C_{2-6}$alkynyl$R^{37}$ (wherein $R^{37}$ is as defined hereinbefore);

12) $C_{2-6}$alkenyl$X^8R^{37}$ (wherein $X^8$ represents —O—, —S—, —SO—, —$SO_2$—, —$NR^{50}CO$—, —$CONR^{51}$—, —$SO_2NR^{52}$—, —$NR^{53}SO_2$— or —$NR^{54}$— (wherein $R^{50}$, $R^{51}$, $R^{52}$, $R^{53}$ and $R^{54}$ each independently represents hydrogen, $C_{1-3}$alkyl or $C_{1-3}$alkoxy$C_{2-3}$alkyl) and $R^{37}$ is as defined hereinbefore);

13) $C_{2-6}$alkynyl$X^9R^{37}$ (wherein $X^9$ represents —O—, —S—, —SO—, —$SO_2$—, —$NR^{55}CO$—, —$CONR^{56}$—, —$SO_2NR^{57}$—, —$NR^{58}SO_2$— or —$NR^{59}$— (wherein $R^{55}$, $R^{56}$, $R^{57}$, $R^{58}$ and $R^{59}$ each independently represents hydrogen, $C_{1-3}$alkyl or $C_{1-3}$alkoxy$C_{2-3}$alkyl) and $R^{37}$ is as defined hereinbefore);

14) $C_{1-3}$alkyl$X^{10}C_{1-3}$alkyl$R^{37}$ (wherein $X^{10}$ represents —O—, —S—, —SO—, —$SO_2$—, —$NR^{60}CO$—, —$CONR^{61}$—, —$SO_2NR^{62}$—, —$NR^{63}SO_2$— or —$NR^{64}$— (wherein $R^{60}$, $R^{61}$, $R^{62}$, $R^{63}$ and $R^{64}$ each independently represents hydrogen, $C_{1-3}$alkyl or $C_{1-3}$alkoxy$C_{2-3}$alkyl) and $R^{37}$ is as defined hereinbefore);

15) $R^{36}$ (wherein $R^{36}$ is as defined hereinbefore); and

16) $C_{1-3}$alkyl$X^{10}C_{1-3}$alkyl$R^{36}$ (wherein $X^{10}$ and $R^{36}$ are as defined hereinbefore), with the proviso that when $R^5$ is bromo, $R^6$ is other than unsubstituted phenyl, methyl substituted phenyl or di-halo substituted phenyl.

2. A compound according to claim 1 wherein $R^6$ is a group —$R^8$—X—$R^9$ where $R^8$, X and $R^9$ are as defined therein.

3. A compound of formula (II)

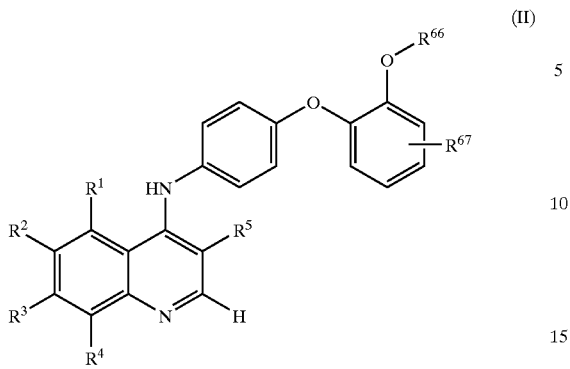

or a pharmaceutically acceptable salt thereof wherein:
$R^1$, $R^2$, $R^3$, $R^4$ are each independently selected from hydrogen, hydroxy, halogeno, cyano, nitro, trifluoromethyl, $C_{1-3}$alkyl, $-NR^{11}R^{12}$ (wherein $R^{11}$ and $R^{12}$, which may be the same or different, each represents hydrogen or $C_{1-3}$alkyl), or a group $R^{13}-X^1-(CH_2)_x$ wherein x is 0 to 3, $X^1$ represents $-O-$, $-CH_2-$, $-OCO-$, carbonyl, $-S-$, $-SO-$, $-SO_2-$, $-NR^{14}CO-$, $-CONR^{15}-$, $-SO_2NR^{16}-$, $-NR^{17}SO_2-$ or $-NR^{18}-$ (wherein $R^{14}$, $R^{15}$, $R^{16}$, $R^{17}$ and $R^{18}$ each independently represents hydrogen, $C_{1-3}$alkyl or $C_{1-3}$alkoxy$C_{2-3}$alkyl) and $R^{13}$ is selected from one of the following sixteen groups:
1) $C_{1-5}$alkyl which may be unsubstituted or which may be substituted with one or more groups selected from hydroxy, fluoro and amino;
2) $C_{1-5}$alkyl$X^2COR^{19}$ (wherein $X^2$ represents $-O-$ or $-NR^{20}-$ (wherein $R^{20}$ represents hydrogen, $C_{1-3}$alkyl or $C_{1-3}$alkoxy$C_{2-3}$alkyl) and $R^{19}$ represents $-NR^{21}R^{22}-$ or $-OR^{23}-$ (wherein $R^{21}$, $R^{22}$ and $R^{23}$ which may be the same or different each represents hydrogen, $C_{1-3}$alkyl or $C_{1-3}$alkoxy$C_{2-3}$alkyl));
3) $C_{1-5}$alkyl$X^3R^{24}$ (wherein $X^3$ represents $-O-$, $-S-$, $-SO-$, $-SO_2-$, $-OCO-$, $-NR^{25}CO-$, $-CONR^{26}-$, $-SO_2NR^{27}-$, $-NR^{28}SO_2-$ or $-NR^{29}-$ (wherein $R^{25}$, $R^{26}$, $R^{27}$, $R^{28}$ and $R^{29}$ each independently represents hydrogen, $C_{1-3}$alkyl or $C_{1-3}$alkoxy$C_{2-3}$alkyl) and $R^{24}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-4}$alkoxy and which cyclic group may bear one or two substituents selected from oxo, hydroxy, halogeno, $C_{1-4}$alkyl, $C_{1-4}$hydroxyalkyl and $C_{1-4}$alkoxy);
4) $C_{1-5}$alkyl$X^4C_{1-5}$alkyl$X^5R^{30}$ (wherein $X^4$ and $X^5$ which may be the same or different are each $-O-$, $-S-$, $-SO-$, $-SO_2-$, $-NR^3CO-$, $-CONR^{32}-$, $-SO_2NR^{33}-$, $-NR^{34}SO_2-$ or $-NR^{35}-$(wherein $R^{31}$, $R^{32}$, $R^{33}$, $R^{34}$ and $R^{35}$ each independently represents hydrogen, $C_{1-3}$alkyl or $C_{1-3}$alkoxy$C_{2-3}$alkyl) and $R^{30}$ represents hydrogen or $C_{1-3}$alkyl);
5) $C_{1-5}$alkyl$R^{36}$ (wherein $R^{36}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy);
6) $(CH_2)_qX^6R^{37}$ (wherein q is an integer from 0 to 5, $X^6$ represents a direct bond, $-O-$, $-S-$, $-SO-$, $-SO_2-$, $-NR^{38}CO-$, $-CONR^{39}-$, $-SO_2NR^{40}-$, $-NR^{41}SO_2-$ or $-NR^{42}-$ (wherein $R^{38}$, $R^{39}$, $R^{40}$, $R^{41}$ and $R^{42}$ each independently represents hydrogen, $C_{1-3}$alkyl or $C_{1-3}$alkoxy$C_{2-3}$alkyl) and $R^{37}$ is a phenyl group, a pyridone group or a 5 or 6 membered aromatic heterocyclic group with 1 to 3 heteroatoms selected from O, N and S, which phenyl, pyridone or aromatic heterocyclic group may carry up to 5 substituents selected from hydroxy, halogeno, amino, $C_{1-4}$alkyl, $C_{1-4}$alkoxy, $C_{1-4}$hydroxyalkyl, $C_{1-4}$hydroxyalkoxy, $C_{1-4}$aminoalkyl, $C_{1-4}$alkylamino, carboxy, cyano, $-CONR^{43}R^{44}$ and $-NR^{45}COR^{46}$ (wherein $R^{43}$, $R^{44}$, $R^{45}$ and $R^{46}$, which may be the same or different, each represents hydrogen, $C_{1-4}$alkyl or $C_{1-3}$alkoxy$C_{2-3}$alkyl));
7) $C_{2-6}$alkenyl$R^{36}$ (wherein $R^{36}$ is as defined hereinbefore);
8) $C_{2-6}$alkynyl$R^{36}$ (wherein $R^{36}$ is as defined hereinbefore);
9) $X^7R^{47}$ (wherein $X^7$ is $-SO_2-$, $-O-$ or $-CONR^{48}R^{49}-$ (wherein $R^{48}$ and $R^{49}$, which may be the same or different, each represents hydrogen, $C_{1-3}$alkyl or $C_{1-3}$alkoxy$C_{2-3}$alkyl) and $R^{47}$ represents $C_{1-5}$alkyl which may be unsubstituted or which may be substituted with one or more groups selected from hydroxy, fluoro and amino) with the provisos that when $X^7$ is $-SO_2-$, $X^1$ is $-O-$, when $X^7$ is $-O-$, $X^1$ is carbonyl, when $X^7$ is $-CONR^{48}R^{49}-$, $X^1$ is $-O-$ or $NR^{18}$ (wherein $R^{48}$, $R^{49}$ and $R^{18}$ are as defined hereinbefore);
10) $C_{2-6}$alkenyl$R^{37}$ (wherein $R^{37}$ is as defined hereinbefore);
11) $C_{2-6}$alkynyl$R^{37}$ (wherein $R^{37}$ is as defined hereinbefore);
12) $C_{2-6}$alkenyl$X^8R^{37}$ (wherein $X^8$ represents $-O-$, $-S-$, $-SO-$, $-SO_2-$, $-NR^{50}CO-$, $-CONR^{51}-$, $-SO_2NR^{52}-$, $-NR^{53}SO_2-$ or $-NR^{54}-$ (wherein $R^{50}$, $R^{51}$, $R^{52}$, $R^{53}$ and $R^{54}$ each independently represents hydrogen, $C_{1-3}$alkyl or $C_{1-3}$alkoxy$C_{2-3}$alkyl) and $R^{37}$ is as defined hereinbefore);
13) $C_{2-6}$alkynyl$X^9R^{37}$ (wherein $X^9$ represents $-O-$, $-S-$, $-SO-$, $-SO_2-$, $-NR^{55}CO-$, $-CONR^{56}-$, $-SO_2NR^{57}-$, $-NR^{58}SO_2-$ or $-NR^{59}-$ (wherein $R^{55}$, $R^{56}$, $R^{57}$, $R^{58}$ and $R^{59}$ each independently represents hydrogen, $C_{1-3}$alkyl or $C_{1-3}$alkoxy$C_{2-3}$alkyl) and $R^{37}$ is as defined hereinbefore);
14) $C_{1-3}$alkyl$X^{10}C_{1-3}$alkyl$R^{37}$ (wherein $X^{10}$ represents $-O-$, $-S-$, $-SO-$, $-SO_2-$, $-NR^{60}CO-$, $-CONR^{61}-$, $-SO_2NR^{62}-$, $-NR^{63}SO_2-$ or $-NR^{64}-$ (wherein $R^{60}$, $R^{61}$, $R^{62}$, $R^{63}$ and $R^{64}$ each independently represents hydrogen, $C_{1-3}$alkyl or $C_{1-3}$alkoxy$C_{2-3}$alkyl) and $R^{37}$ is as defined hereinbefore);
15) $R^{36}$ (wherein $R^{36}$ is as defined hereinbefore); and
16) $C_{1-3}$alkyl$X^{10}C_{1-3}$alkyl$R^{36}$ (wherein $X^{10}$ and $R^{36}$ are as defined hereinbefore);
$R^5$ is chloro or bromo;
$R^{66}$ is $C_{1-6}$ alkyl and $R^{67}$ is selected from hydrogen, halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino.

4. A compound of formula (IB)

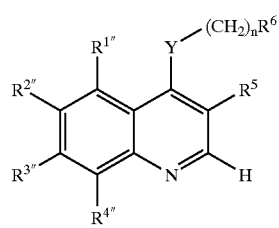

(IB)

wherein:

n is 0–1;

Y is selected from —NH—; $R^5$ is chloro or bromo;

$R^6$ is cycloalkyl of 3 to 7 carbon atoms, which may be optionally substituted with one or more alkyl of 1 to 6 carbon atom groups; or is a pyridinyl, pyrimidinyl, or phenyl ring; wherein the pyridinyl, pyrimidinyl, or phenyl ring may be substituted with one, two or three groups selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenyl, benzoyl, amino, alkylamino of 1–6 carbon atoms, dialkylamino of 2 to 12 carbon atoms, alkanoylamino of 1–6 carbon atoms, alkenoylamino of 3–8 carbon atoms, alkynoylamino of 3–8 carbon atoms, and benzoylamino; or two adjacent substituents on said phenyl, pyridyl or pyrimidinyl ring may be joined together as a 5-membered heterocyclic ring having one or two nitrogen atoms, to form a fused ring;

or $R^6$ is a group —$R^8$—X—$R^9$ where $R^8$ is a divalent cycloalkyl of 3 to 7 carbon atoms, which may be optionally further substituted with one or more alkyl of 1 to 6 carbon atom groups; or is a divalent pyridinyl, pyimidinyl, or phenyl ring; wherein the pyridinyl, pyrimidinyl, or phenyl ring may be optionally further substituted with one or more groups selected from halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino;

where X is selected from $CH_2$, —NH—, —O—, —S—, $CH_2$ or —$NR^5$— where $R^5$ is alkyl of 1–6 carbon atoms, and $R^9$ is a group $(CH_2)_m R^{10}$ where m is 0, or an integer of from 1–3 and $R^{10}$ is an optionally substituted aryl or optionally substituted cycloalkyl ring of up to 10 carbon atoms, or $R^{10}$ is a heterocyclic ring containing 1 or 2 oxygen atoms and optionally one or more substitutents;

at least one of $R^{1''}$, $R^{2''}$, $R^{3''}$ or $R^{4''}$ is a group $R^{13'}$—$X^1$—$(CH_2)_x$ wherein x is 0 to 3, $X^1$ represents —O—, —$CH_2$—, —OCO—, carbonyl, —S—, —SO—, —$SO_2$—, —$NR^{14}CO$—, —$CONR^{15}$—, —$SO_2NR^{16}$—, —$NR^{17}SO_2$— or —$NR^{18}$— (wherein $R^{14}$, $R^{15}$, $R^{16}$, $R^{17}$ and $R^{18}$ each independently represents hydrogen, $C_{1-3}$alkyl or $C_{1-3}$alkoxy$C_{2-3}$alkyl), and $R^{13'}$ is alkyl substituted by chloro or bromo;

and the remainder of groups $R^{1''}$, $R^{2''}$, $R^{3''}$ or $R^{4''}$ are each independently selected from hydrogen, hydroxy, halogeno, cyano, nitro, trifluoromethyl, $C_{1-3}$alkyl, —$NR^{11}R^{12}$ (wherein $R^{11}$ and $R^{12}$, which may be the same or different, each represents hydrogen or $C_{1-3}$alkyl), or a group $R^{13}$—$X^1$—$(CH_2)_x$ wherein x is 0 to 3, $X^1$ represents —O—, —$CH_2$—, —OCO—, carbonyl, —S—, —SO—, —$SO_2$—, —$NR^{14}CO$—, —$CONR^{15}$—, —$SO_2NR^{16}$—, —$NR^{17}SO_2$— or —$NR^{18}$— (wherein $R^{14}$, $R^{15}$, $R^{16}$, $R^{17}$ and $R^{18}$ each independently represents hydrogen, $C_{1-3}$alkyl or $C_{1-3}$alkoxy$C_{2-3}$alkyl) and $R^{13}$ is selected from one of the following sixteen groups:

1) $C_{1-5}$alkyl which may be unsubstituted or which may be substituted with one or more groups selected from hydroxy, fluoro and amino;

2) $C_{1-5}$alkyl$X^2COR^{19}$ (wherein $X^2$ represents —O— or —$NR^{20}$— (wherein $R^{20}$ represents hydrogen, $C_{1-3}$alkyl or $C_{1-3}$alkoxy$C_{2-3}$alkyl) and $R^{19}$ represents —$NR^{21}R^{22}$— or —$OR^{23}$—(wherein $R^{21}$, $R^{22}$ and $R^{23}$ which may be the same or different each represents hydrogen, $C_{1-3}$alkyl or $C_{1-3}$alkoxy$C_{2-3}$alkyl));

3) $C_{1-5}$alkyl$X^3R^{24}$ (wherein $X^3$ represents —O—, —S—, —SO—, —$SO_2$—, —OCO—, —$NR^{25}CO$—, —$CONR^{26}$—, —$SO_2NR^{27}$—, —$NR^{28}SO_2$— or —$NR^{29}$— (wherein $R^{25}$, $R^{26}$, $R^{27}$, $R^{82}$ and $R^{29}$ each independently represents hydrogen, $C_{1-3}$alkyl or $C_{1-3}$alkoxy$C_{2-3}$alkyl) and $R^{24}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-4}$alkoxy and which cyclic group may bear one or two substituents selected from oxo, hydroxy, halogeno, $C_{1-4}$alkyl, $C_{1-4}$hydroxyalkyl and $C_{1-4}$alkoxy);

4) $C_{1-5}$alkyl$X^4C_{1-5}$alkyl$X^5R^{30}$ (wherein $X^4$ and $X^5$ which may be the same or different are each —O—, —S—, —SO—, —$SO_2$—, —$NR^{31}CO$—, —$CONR^{32}$—, —$SO_2NR^{33}$—, —$NR^{34}SO_2$— or —$NR^{35}$— (wherein $R^{31}$, $R^{32}$, $R^{33}$, $R^{34}$ and $R^{35}$ each independently represents hydrogen, $C_{1-3}$alkyl or $C_{1-3}$alkoxy$C_{2-3}$alkyl) and $R^{30}$ represents hydrogen or $C_{1-3}$alkyl);

5) $C_{1-5}$alkyl$R^{36}$ (wherein $R^{36}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy);

6) $(CH_2)_qX^6R^{37}$ (wherein q is an integer from 0 to 5, $X^6$ represents a direct bond, —O—, —S—, —SO—, —SO$_2$—, —NR$^{38}$CO—, —CONR$^{39}$—, —SO$_2$NR$^{40}$—, —NR$^{41}$SO$_2$— or —NR$^{42}$— (wherein $R^{38}$, $R^{39}$, $R^{40}$, $R^{41}$ and $R^{42}$ each independently represents hydrogen, $C_{1-3}$alkyl or $C_{1-3}$alkoxy$C_{2-3}$alkyl) and $R^{37}$ is a phenyl group, a pyridone group or a 5 or 6 membered aromatic heterocyclic group with 1 to 3 heteroatoms selected from O, N and S, which phenyl, pyridone or aromatic heterocyclic group may carry up to 5 substituents selected from hydroxy, halogeno, amino, $C_{1-4}$alkyl, $C_{1-4}$alkoxy, $C_{1-4}$hydroxyalkyl, $C_{1-4}$hydroxyalkoxy, $C_{1-4}$aminoalkyl, $C_{1-4}$alkylamino, carboxy, cyano, —CONR$^{43}$R$^{44}$ and —NR$^{45}$COR$^{46}$ (wherein $R^{43}$, $R^{44}$, $R^{45}$ and $R^{46}$, which may be the same or different, each represents hydrogen, $C_{1-4}$alkyl or $C_{1-3}$alkoxy$C_{2-3}$alkyl));

7) $C_{2-6}$alkenyl$R^{36}$ (wherein $R^{36}$ is as defined hereinbefore);

8) $C_{2-6}$alkynyl$R^{36}$ (wherein $R^{36}$ is as defined hereinbefore);

9) $X^7R^{47}$ (wherein $X^7$ is —SO$_2$—, —O— or —CONR$^{48}$R$^{49}$— (wherein $R^{48}$ and $R^{49}$, which may be the same or different, each represents hydrogen, $C_{1-3}$alkyl or $C_{1-3}$alkoxy$C_{2-3}$alkyl) and $R^{47}$ represents $C_{1-5}$alkyl which may be unsubstituted or which may be substituted with one or more groups selected from hydroxy, fluoro and amino) with the provisos that when $X^7$ is —SO$_2$—, $X^1$ is —O—, when $X^7$ is —O—, $X^1$ is carbonyl, when $X^7$ is —CONR$^{48}$R$^{49}$—, $X^1$ is —O— or NR$^{18}$ (wherein $R^{48}$, $R^{49}$ and $R^{18}$ are as defined hereinbefore);

10) $C_{2-6}$alkenyl$R^{37}$ (wherein $R^{37}$ is as defined hereinbefore);

11) $C_{2-6}$alkynyl$R^{37}$ (wherein $R^{37}$ is as defined hereinbefore);

12) $C_{2-6}$alkenyl$X^8R^{37}$ (wherein $X^8$ represents —O—, —S—, —SO—, —SO$_2$—, —NR$^{50}$CO—, —CONR$^{51}$—, —SO$_2$NR$^{52}$—, —NR$^{53}$SO$_2$— or —NR$^{54}$— (wherein $R^{50}$, $R^{51}$, $R^{52}$, $R^{53}$ and $R^{54}$ each independently represents hydrogen, $C_{1-3}$alkyl or $C_{1-3}$alkoxy$C_{2-3}$alkyl) and $R^{37}$ is as defined hereinbefore);

13) $C_{2-6}$alkynyl$X^9R^{37}$ (wherein $X^9$ represents —O—, —S—, —SO—, —SO$_2$—, —NR$^{55}$CO—, —CONR$^{56}$—, —SO$_2$NR$^{57}$—, —NR$^{58}$SO$_2$— or —NR$^{59}$— (wherein $R^{55}$, $R^{56}$, $R^{57}$, $R^{58}$ and $R^{59}$ each independently represents hydrogen, $C_{1-3}$alkyl or $C_{1-3}$alkoxy$C_{2-3}$alkyl) and $R_{37}$ is as defined hereinbefore);

14) $C_{1-3}$alkyl$X^{10}C_{1-3}$alkyl$R^{37}$ (wherein $X^{10}$ represents —O—, —S—, —SO—, —SO$_2$—, —NR$^{60}$CO—, —CONR$^{61}$—, —SO$_2$NR$^{62}$—, —NR$^{63}$SO$_2$— or —NR$^{64}$— (wherein $R^{60}$, $R^{61}$, $R^{62}$, $R^{63}$ and $R^{64}$ each independently represents hydrogen, $C_{1-3}$alkyl or $C_{1-3}$alkoxy$C_{2-3}$alkyl) and $R^{37}$ is as defined hereinbefore);

15) $R^{36}$ (wherein $R^{36}$ is as defined hereinbefore); and

16) $C_{1-3}$alkyl$X^{10}C_{1-3}$alkyl$R^{36}$ (wherein $X^{10}$ and $R^{36}$ are as defined hereinbefore).

5. A process for preparing a compound of formula (IA) as defined in claim 1, which process comprises reacting a compound of formula (III)

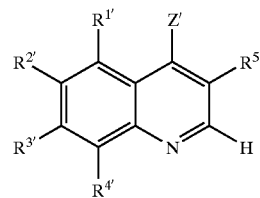

(III)

where $R^{1'}$, $R^{2'}$, $R^{3'}$, $R^{4'}$ represent $R^1$, $R^2$, $R^3$ and $R^4$ respectively as defined in claim 1 or a precursor thereof, $R^5$ is as defined in claim 1, and Z' is a leaving group, with a compound of formula (IV)

$$H—Y(CH_2)_nR^{6'} \qquad (IV)$$

where Y, X, and n are as defined in claim 1, and $R^{6'}$ is a group $R^6$ as defined in claim 1 or a precursor thereof; and thereafter if necessary or desired converting precursor groups $R^{1'}$, $R^{2'}$, $R^{3'}$, $R^{4'}$ and $R^{6'}$ to groups of formula $R^1$, $R^2$, $R^3$, $R^4$ and $R^6$ respectively, or converting a group $R^1$, $R^2$, $R^3$, $R^4$ and $R^6$ to a different such group.

6. A compound of formula (I)

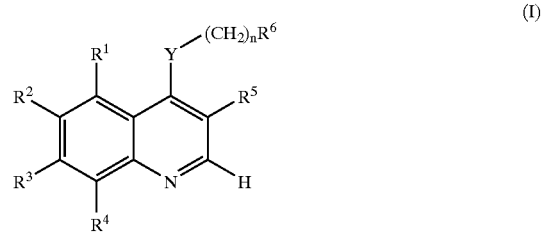

(I)

or a pharmaceutically acceptable salt thereof wherein:

n is 0–1;

Y is selected from —NH—;

$R^5$ is chloro or bromo;

$R^6$ is cycloalkyl of 3 to 7 carbon atoms, which may be optionally substituted with one or more alkyl of 1 to 6 carbon atom groups; or is a pyridinyl, pyrimidinyl, or phenyl ring; wherein the pyridinyl, pyrimidinyl, or phenyl ring may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino;

or $R^6$ is a group —$R^8$—X—$R^9$ where $R^8$ is a divalent cycloalkyl of 3 to 7 carbon atoms, which may be optionally further substituted with one or more alkyl of 1 to 6 carbon atom groups; or is a divisent pyridinyl, pyimidinyl, or phenyl ring; wherein the pyridinyl, pyrimidinyl, or phenyl ring may be optionally further substituted with one or more groups selected from halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino;

where X is selected from —NH—, —O—, —S—, $CH_2$ or —$NR^a$— where $R^a$ is alkyl of 1–6 carbon atoms, and $R^9$ is a group $(CH_2)_m R^{10}$ where m is 0, or an integer of from 1-3 and $R^{10}$ is an optionally substituted aryl or optionally substituted cycloalkyl ring of up to 10 carbon atoms, or $R^{10}$ is a heterocyclic ring containing 1 or 2 oxygen atoms and optionally one or more substitutents;

$R^1$, $R^2$, $R^3$ and $R^4$ are each independently selected from hydrogen, hydroxy, halogeno, cyano, nitro, trifluoromethyl, $C_{1-3}$alkyl, —$NR^{11}R^{12}$ (wherein $R^{11}$ and $R^{12}$, which may be the same or different, each represents hydrogen or $C_{1-3}$alkyl), or a group $R^{13}$—$X^1$—$(CH_2)_x$ wherein x is 0 to 3, $X^1$ represents —O—, —$CH_2$—, —OCO—, carbonyl, —S—, —SO—, —$SO_2$—, —$NR^{14}CO$—, —$SO_2NR^{16}$—, —$NR^{17}SO_2$— or —$NR^{18}$— (wherein $R^{14}$, $R^{16}$, $R^{17}$ and $R^{18}$ each independently represents hydrogen, $C_{1-3}$alkyl or $C_{1-3}$alkoxyC2-3alkyl) and $R^{13}$ is selected from one of the following sixteen groups:

1) $C_{1-5}$alkyl which may be unsubstituted or which may be substituted with one or more groups selected from hydroxy, fluoro and amino;

2) $C_{1-5}$alkyl$X^2COR^{19}$ (wherein $X^2$ represents —O— or —$NR^{20}$— (wherein $R^{20}$ represents hydrogen, $C_{1-3}$alkyl or $C_{1-3}$alkoxyC_{2-3}alkyl) and $R^{19}$ represents —$NR^{21}R^{22}$— or —$OR^{23}$— (wherein $R^{21}$, $R^{22}$ and $R^{23}$ which may be the same or different each represents hydrogen, $C_{1-3}$alkyl or $C_{1-3}$alkoxyC_{2-3}alkyl));

3) $C_{1-5}$alkyl$X^3R^{24}$ (wherein $X^3$ represents —O—, —S—, —SO—, —$SO_2$—, —OCO—, —$NR^{25}CO$—, —$CONR^{26}$—, —$SO_2NR^{27}$—, —$NR^{28}SO_2$— or —$NR^{29}$— (wherein $R^{25}$, $R^{26}$, $R^{27}$, $R^{28}$ and $R^{29}$ each independently represents hydrogen, $C_{1-3}$alkyl or $C_{1-3}$alkoxyC_{2-3}alkyl) and $R^{24}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-4}$alkoxy and which cyclic group may bear one or two substituents selected from oxo, hydroxy, halogeno, $C_{1-4}$alkyl, $C_{1-4}$hydroxyalkyl and $C_{1-4}$alkoxy);

4) $C_{1-5}$alkyl$X^4C_{1-5}$alkyl$X^5R^{30}$ (wherein $X^4$ and $X^5$ which may be the same or different are each —O—, —S—, —SO—, —$SO_2$—, —$NR^{31}CO$—, —$CONR^{32}$—, —$SO_2NR^{33}$—, —$NR^{34}SO_2$— or —$NR^{35}$—(wherein $R^{31}$, $R^{32}$, $R^{33}$, $R^{34}$ and $R^{35}$ each independently represents hydrogen, $C_{1-3}$alkyl or $C_{1-3}$alkoxyC_{2-3}alkyl) and $R^{30}$ represents hydrogen or $C_{1-3}$alkyl);

5) $C_{1-5}$alkyl$R^{36}$ (wherein $R^{36}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy);

6) $(CH_2)_qX^6R^{37}$ (wherein q is an integer from 0 to 5, $X^6$ represents a direct bond, —O—, —S—, —SO—, —$SO_2$—, —$NR^{38}CO$—, —$CONR^{39}$—, —$SO_2NR^{40}$—, —$NR^{41}SO_2$— or —$NR^{42}$— (wherein $R^{38}$, $R^{39}$, $R^{40}$, $R^{41}$ and $R^{42}$ each independently represents hydrogen, $C_{1-3}$alkyl or $C_{1-3}$alkoxyC_{2-3}alkyl) and $R^{37}$ is a phenyl group, a pyridone group or a 5 or 6 membered aromatic heterocyclic group with 1 to 3 heteroatoms selected from O, N and S, which phenyl, pyridone or aromatic heterocyclic group may carry up to 5 substituents selected from hydroxy, halogeno, amino, $C_{1-4}$alkyl, $C_{1-4}$alkoxy, $C_{1-4}$hydroxyalkyl, $C_{1-4}$hydroxyalkoxy, $C_{1-4}$aminoalkyl, $C_{1-4}$alkylamino, carboxy, cyano, —$CONR^{43}R^{44}$ and —$NR^{45}COR^{46}$ (wherein $R^{43}$, $R^{44}$, $R^{45}$ and $R^{46}$, which may be the same or different, each represents hydrogen, $C_{1-4}$alkyl or $C_{1-3}$alkoxyC_{2-3}alkyl));

7) $C_{2-6}$alkenyl$R^{36}$ (wherein $R^{36}$ is as defined hereinbefore);

8) $C_{2-6}$alkynyl$R^{36}$ (wherein $R^{36}$ is as defined hereinbefore);

9) $X^7R^{47}$ (wherein $X^7$ is —$SO_2$—, —O— or —$CONR^{48}R^{49}$— (wherein $R^{48}$ and $R^{49}$, which may be the same or different, each represents hydrogen, $C_{1-3}$alkyl or $C_{1-3}$alkoxyC_{2-3}alkyl) and $R^{47}$ represents $C_{1-5}$alkyl which may be unsubstituted or which may be substituted with one or more groups selected from hydroxy, fluoro and amino) with the provisos that when $X^7$ is —$SO_2$—, $X^1$ is —O—, when $X^7$ is —O—, $X^1$ is carbonyl, when $X^7$ is —$CONR^{48}R^{49}$—, $X^1$ is —O— or $NR^{18}$ (wherein $R^{48}$, $R^{49}$ and $R^{18}$ are as defined hereinbefore);

10) $C_{2-6}$alkenyl$R^{37}$ (wherein $R^{37}$ is as defined hereinbefore);

11) $C_{2-6}$alkynyl$R^{37}$ (wherein $R^{37}$ is as defined hereinbefore);

12) $C_{2-6}$alkenyl$X^8R^{37}$ (wherein $X^8$ represents —O—, —S—, —SO—, —$SO_2$—, —$NR^{50}CO$—, —$CONR^{51}$—, —$SO_2NR^{52}$—, —$NR^{53}SO_2$— or —$NR^{54}$—(wherein $R^{50}$, $R^{51}$, $R^{52}$, $R^{53}$ and $R^{54}$ each independently represents hydrogen, $C_{1-3}$alkyl or $C_{1-3}$alkoxyC_{2-3}alkyl) and $R^{37}$ is as defined hereinbefore);

13) $C_{2-6}$alkynyl$X^9R^{37}$ (wherein $X^9$ represents —O—, —S—, —SO—, —$SO_2$—, —$NR^{55}CO$—, —$CONR^{56}$—, —$SO_2NR^{57}$—, —$NR^{58}SO_2$— or —$NR^{59}$— (wherein $R^{55}$, $R^{56}$, $R^{57}$, $R^{58}$ and $R^{59}$ each independently represents hydrogen, $C_{1-3}$alkyl or $C_{1-3}$alkoxyC_{2-3}alkyl) and $R^{37}$ is as defined hereinbefore);

14) $C_{1-3}$alkyl$X^{10}C_{1-3}$alkyl$R^{37}$ (wherein $X^{10}$ represents —O—, —S—, —SO—, —$SO_2$—, —$NR^{60}CO$—, —$CONR^{61}$—, —$SO_2NR^{62}$—, —$NR^{63}SO_2$— or —$NR^{64}$— (wherein $R^{60}$, $R^{61}$, $R^{62}$, $R^{63}$ and $R^{64}$ each independently represents hydrogen, $C_{1-3}$alkyl or $C_{1-3}$alkoxyC_{2-3}alkyl) and $R^{37}$ is as defined hereinbefore);

15) $R^{36}$ (wherein $R^{36}$ is as defined hereinbefore); and
16) $C_{1-3}alkylX^{10}C_{1-3}alkylR^{36}$ (wherein $X^{10}$ and $R^{36}$ are as defined hereinbefore), with the proviso that when $R^5$ is bromo, $R^6$ is other than unsubstituted phenyl, methyl substituted phenyl or di-halo substituted phenyl.

7. A pharmaceutical composition comprising a compound as claimed in any one of claims 2, 3, 4, 1 and 6 in combination with a pharmaceutically acceptable carrier or excipient.

* * * * *